US012133993B2

(12) United States Patent
Novosad et al.

(10) Patent No.: US 12,133,993 B2
(45) Date of Patent: Nov. 5, 2024

(54) REAL-TIME ANATOMIC POSITION MONITORING IN RADIOTHERAPY USING MACHINE LEARNING REGRESSION

(71) Applicant: Elekta, Inc., Atlanta, GA (US)

(72) Inventors: Philip P. Novosad, Montreal (CA); Silvain Beriault, Longueuil (CA)

(73) Assignee: Elekta, Inc., Atlanta, GA (US)

( * ) Notice: Subject to any disclaimer, the term of this patent is extended or adjusted under 35 U.S.C. 154(b) by 696 days.

(21) Appl. No.: 17/302,252

(22) Filed: Apr. 28, 2021

(65) Prior Publication Data
US 2022/0347493 A1 Nov. 3, 2022

(51) Int. Cl.
*A61N 5/10* (2006.01)
*G06T 7/33* (2017.01)

(52) U.S. Cl.
CPC ......... *A61N 5/1068* (2013.01); *A61N 5/1049* (2013.01); *G06T 7/337* (2017.01);
(Continued)

(58) Field of Classification Search
CPC ...... A61N 5/00; A61N 5/1039; A61N 5/1037; A61N 5/1067; A61N 5/1081; A61N 5/10; A61N 5/103; A61N 5/1049; A61N 5/1038; A61N 5/1068; A61N 2005/1041; A61N 2005/1055; A61N 2005/1091; A61N 2005/1061; G06N 20/10; G06T 7/337;
(Continued)

(56) References Cited

U.S. PATENT DOCUMENTS 11,679,276 B2  6/2023  Novosad et al.
2009/0022379 A1  1/2009  Tashiro et al.
(Continued)

FOREIGN PATENT DOCUMENTS

| CN | 117377516 | 1/2024 |
|---|---|---|
| WO | 2020077198 | 4/2020 |
| WO | 2022232749 | 11/2022 |

OTHER PUBLICATIONS

"International Application Serial No. PCT US2022 071772, International Preliminary Report on Patentability mailed Nov. 9, 2023", 22 pgs.

(Continued)

*Primary Examiner* — Jurie Yun
(74) *Attorney, Agent, or Firm* — Schwegman Lundberg & Woessner, P.A.

(57) ABSTRACT

Systems and methods are disclosed for monitoring anatomic position of a human subject for a radiotherapy treatment session, based on use of a regression model trained to estimate movement of a region of interest based on 2D image data input. Example operations for movement estimation include: obtaining 3D image data for a subject, which provides a reference volume and at least one defined region of interest; obtaining 2D image data corresponding to the subject, captured in real time (during the radiotherapy treatment session); extracting features from the 2D image data; analyzing the extracted features with a machine learning regression model, trained to estimate a spatial transformation in the three dimensions of the reference volume; and outputting and using a relative motion estimation of the at least one region of interest, produced from the machine learning regression model, the relative motion estimation being estimated from the extracted features.

23 Claims, 14 Drawing Sheets

(52) U.S. Cl.
CPC ............... *A61N 2005/1055* (2013.01); *A61N 2005/1091* (2013.01); *G06T 2207/10081* (2013.01); *G06T 2207/10088* (2013.01); *G06T 2207/20081* (2013.01); *G06T 2207/30096* (2013.01)

(58) Field of Classification Search
CPC ............. G06T 7/33; G06T 2207/10081; G06T 2207/10088; G06T 2207/20081; G06T 2207/30096
See application file for complete search history.

(56) References Cited

U.S. PATENT DOCUMENTS

| | | |
|---|---|---|
| 2018/0043182 A1 | 2/2018 | Wu et al. |
| 2020/0258227 A1 | 8/2020 | Liao et al. |
| 2021/0046327 A1 | 2/2021 | Bériault et al. |
| 2021/0046331 A1 | 2/2021 | Lachaine et al. |
| 2022/0347490 A1 | 11/2022 | Novosad et al. |

OTHER PUBLICATIONS

"International Application Serial No. PCT US2022 071772, International Search Report mailed Jun. 16, 2022", 3 pgs.

"International Application Serial No. PCT US2022 071772, Written Opinion mailed Jun. 16, 2022", 20 pgs.

"U.S. Appl. No. 17/302,254, Non Final Office Action mailed Oct. 25, 2022", 10 pgs.

"U.S. Appl. No. 17/302,254, Response filed Jan. 25, 2023 to Non Final Office Action mailed Oct. 25, 2022", 14 pgs.

"U.S. Appl. No. 17/302,254, Notice of Allowance mailed Feb. 22, 2023", 10 pgs.

"European Application Serial No. 22796941.7, Extended European Search Report mailed Aug. 5, 2024", 9 pgs.

Li, Feng, "Tracking Lung Tumors in Orthogonal X-Rays", Computational and Mathematical Methods in Medicine, vol. 2013, (Nov. 15, 2013), 1-7.

Ran, Wei, "Convolutional Neural Network (CNN) Based Three Dimensional Tumor Localization Using Single X-Ray Projection", IEEE Access, vol. 7, [retrieved on Apr. 1, 2019], (Feb. 14, 2019), 37026-37038.

REAL-TIME ANATOMIC POSITION MONITORING IN RADIOTHERAPY USING MACHINE LEARNING REGRESSION

TECHNICAL FIELD

Embodiments of the present disclosure pertain generally to medical image and artificial intelligence processing techniques used in connection with a radiation therapy planning and treatment system. In particular, the present disclosure pertains to using machine learning technologies to estimate anatomic position and movement of a human subject during a radiation therapy session.

BACKGROUND

Radiation therapy (or "radiotherapy") can be used to treat cancers or other ailments in mammalian (e.g., human and animal) tissue. One such radiotherapy technique is provided using a Gamma Knife, by which a patient is irradiated by a large number of low-intensity gamma rays that converge with high intensity and high precision at a target (e.g., a tumor). Another such radiotherapy technique is provided using a linear accelerator (LINAC), whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs).

In radiotherapy, treatment planning is typically performed based on medical images of a patient and requires the delineation of target volumes and normal critical organs in the medical images. One challenge occurs with accurately tracking the various objects, such as a tumor, healthy tissue, or other aspects of patient anatomy when the patient is moving (e.g., breathing). This challenge arises because full three-dimensional patient motion occurring during radiotherapy treatment cannot be directly measured in real-time with current imaging hardware. On both conventional LINAC and MR-LINAC systems, the scan time for acquiring volumetric 3D images (e.g., 3D CBCT or 3D MRI images) is too long to capture respiratory motion of a human subject with sufficient temporal resolution, even with recent advances in artificial intelligence (AI) processing and compressed sensing.

Some imaging techniques have been developed to estimate the relative motion of an object contained in a specified region of interest, i.e. relative to a reference volume, which contains auxiliary information such as contoured regions of interest or the dose plan. For instance, the underlying 3D patient motion may be estimated (inferred) from instantaneous partial measurements, using from 2D images acquired in real-time. Some of these estimation techniques use 2D kV projections or 2D MRI slices to determine an estimate of movement in two-dimensional planes, but are limited because 2D images are not able to fully track the movement of the various objects in three dimensions.

Other motion estimation techniques used with radiotherapy rely on detecting surface information that is indicative of patient movement, such as with sensors that are placed directly on a patient, or by tracking markers on a vest or a box affixed to the patient. However, these techniques assume that the surface information is correlated to internal patient state, which often is not accurate. As a result, some anatomic position monitoring and motion estimates may be incomplete or incorrect.

Overview

In some embodiments, methods, systems, and computer-readable mediums are provided for monitoring anatomic position and movement of a human subject during a radiotherapy treatment session. In various examples, operations for monitoring anatomic position include: obtaining three-dimensional image data corresponding to the subject, the three-dimensional image data including: a reference volume that represents the patient anatomy in three dimensions, and at least one region of interest defined within the three dimensions; obtaining two-dimensional image data corresponding to the subject, the two-dimensional image data captured during the radiotherapy treatment session, and the two-dimensional image data capturing at least a portion of the region of interest; extracting features from the two-dimensional image data; providing the extracted features as input to a machine learning regression model, the machine learning regression model trained to estimate a spatial transformation in the three dimensions of the reference volume from features extracted from two-dimensional image data; and obtaining, from output of the machine learning regression model, a relative motion estimation of the at least one region of interest, with the relative motion estimation indicating motion of the at least one region of interest relative to the reference volume, as estimated from the extracted features.

In further examples, the two-dimensional image data (e.g., captured in real time) comprises a first two-dimensional image captured at a first orientation and a second two-dimensional image captured at a second orientation. For instance, the first two-dimensional image is captured from a first plane, and the second two-dimensional image is captured from a second plane that is orthogonal to the first plane. Also, the first two-dimensional image may be captured at a first time during the radiotherapy treatment session and the second two-dimensional image may be captured at a second time during the radiotherapy treatment session. For instance, the second time may occur within 300 milliseconds after the first time.

Also in further examples, features extracted from the two-dimensional image data include a first set of features extracted from the first two-dimensional image and a second set of features extracted from the second two-dimensional image. The first set of features and the second set of features may be combined into a multi-dimensional feature vector, and the machine learning regression model is trained to process the multi-dimensional feature vector as input. Further, the extracting of the first set of features and the second set of features may include extracting respective features within the at least one region of interest. Additionally, the extracting of the respective features within the at least one region of interest may include performing deformable image registration, and performing dimensionality reduction techniques.

Also in further examples, the three-dimensional image data is captured prior to the radiotherapy treatment session, and the three-dimensional image data comprises a three-dimensional magnetic resonance (MR) volume or a three-dimensional computed tomography (CT) volume. Additionally, the first and second two-dimensional images may be kilovoltage (kV) x-ray projection images, and extracting the first set of features and the second set of features comprises extracting fiducial positions from the respective kV x-ray projection images. With either of these examples, a training process may include training the machine learning regression model prior to the radiotherapy treatment session, with the training further including fitting the regression model with a mapping identified between pairs of image transformation parameters and corresponding multi-orientation features (e.g., extracted from the volumes captured prior to the radiotherapy treatment session).

In a specific example, the two-dimensional image data includes magnetic resonance (MR) imaging data, as the reference volume is acquired with a first MR pulse acquisition sequence and the two-dimensional image data is acquired with a second MR pulse acquisition sequence. For instance, use of multiple imaging contrasts may include capturing an intermediate three-dimensional reference volume using the second MR pulse acquisition sequence, prior to the radiotherapy treatment session; and performing a registration of the intermediate three-dimensional reference volume to the reference volume; the relevant training of the machine learning regression model includes use of this registration, and analysis of the extracted features includes use this registration. In another example, use of multiple imaging contrasts includes obtaining image templates from additional two-dimensional image data corresponding to the subject, the additional two-dimensional image data obtained using the second MR pulse acquisition sequence prior to the radiotherapy treatment session; performing a registration of the image templates to the reference volume, to determine an offset between the image templates and the reference volume; and modifying the three-dimensional image data based on the offset, such that the machine learning regression model is trained to use regression with the modified three-dimensional image data. Then, extracting features from the two-dimensional image data may include use of the image templates as registration targets for feature extraction; further, the relative motion estimation of the at least one region of interest may include use of the offset.

Based on the results of the motion estimation, further operations may include performing a radiotherapy treatment with a radiotherapy machine, using the relative motion estimation of the region of interest. Performing the radiotherapy treatment may include one or more of: changing a position of a radiotherapy beam from the radiotherapy machine, based on the relative motion estimation; changing a shape of a radiotherapy beam from the radiotherapy machine, based on the relative motion estimation; gating a radiotherapy beam (e.g., stopping an output of the radiotherapy beam, or starting an output of the radiotherapy beam), based on the relative motion estimation. Other variations or operations may also be triggered or affected by the resulting motion estimation.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
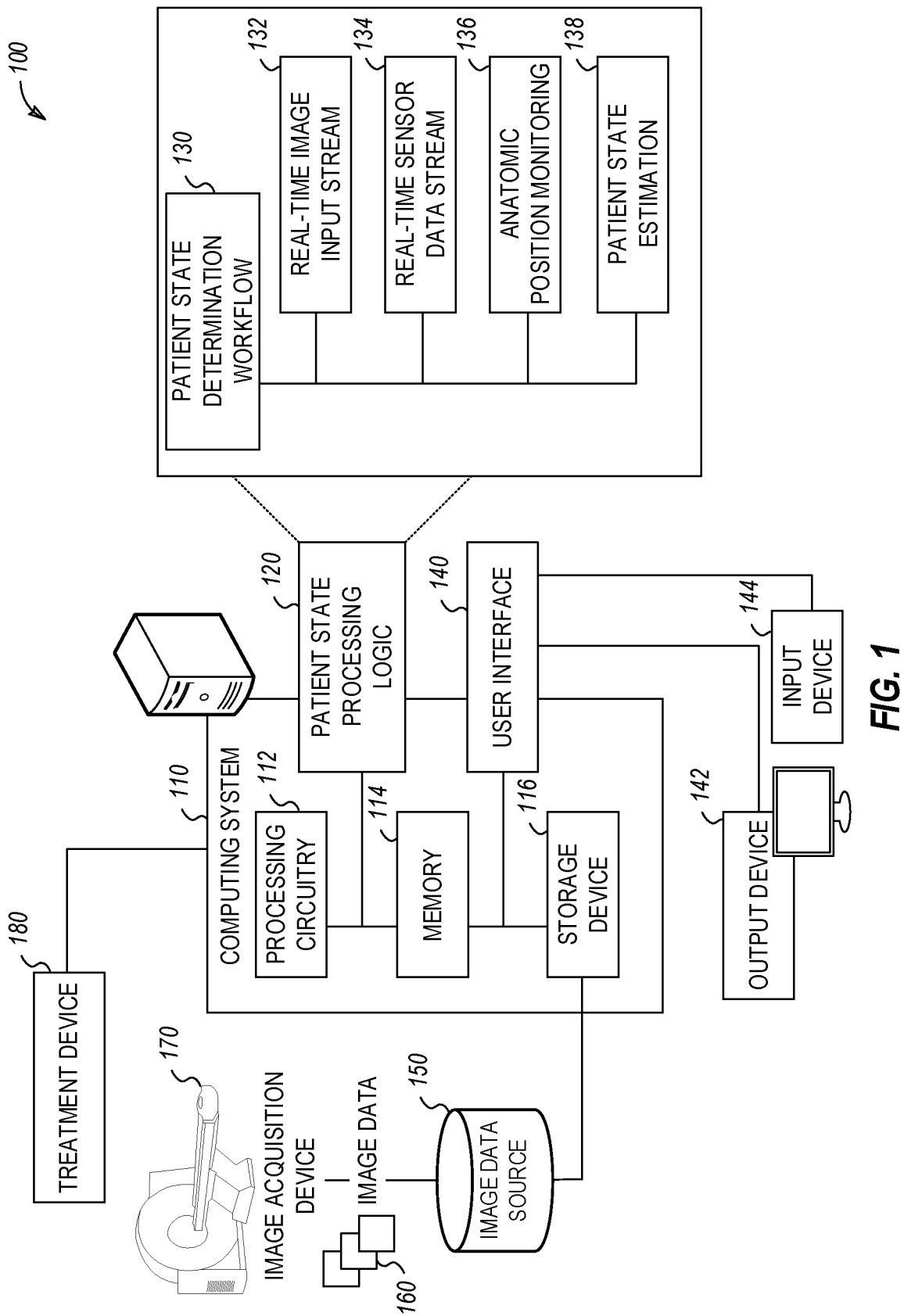
FIG. 1 illustrates a radiotherapy system, according to some examples.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not to be taken in a limiting sense, and the scope of the present disclosure is defined by the appended claims and their equivalents.

The following discusses various implementations of an anatomic position monitoring (APM) technique usable in radiotherapy or radiosurgery applications. In an example, this APM technique may be used to track, in real-time, the motion of an object contained in a specified region of interest. This APM technique includes the analysis of 2D images, captured on an ongoing basis, with a trained regression model. This trained regression model generates estimated transformation parameters that are used to infer the true 3D motion of a specified region of interest (and related anatomical structure).

In the examples discussed herein, features are extracted from one or more 2D images captured of a patient, and analyzed with the trained regression model. This machine learning regression model is trained on different types and characteristics of image transformation and image features, generated from a 3D reference volume of imaging data captured from the same patient. In turn, the extracted features are used to estimate an image transformation describe the movement of a region of interest within the 3D volume. The movement of this region of interest, within a 3D space, may be used for a variety of radiotherapy treatment adaptations.

In conventional radiotherapy techniques, larger margins are often used to account for motion due to breathing, etc. With image guided radiation therapy (IGRT) it is possible to obtain more accurate targeting, therefore margins can be reduced. IGRT may use computed tomography (CT) imaging, cone beam CT (CBCT), magnetic resonance (MR) imaging, positron-emission tomography (PET) imaging, or the like to obtain a 3D or 4D image of a patient prior to irradiation. For example, a CBCT-enabled LINAC (linear accelerator) may consist of a kV source/detector affixed to the gantry at a 90 degree angle to a radiation beam, or a MR-LINAC device may consist of a LINAC integrated directly with a magnetic resonance (MR) scanner. Localizing the motion of the human subject during the actual irradiation treatment delivery (intrafraction motion) may allow reduction of additional treatment margins that would otherwise be used to encompass motion.

Conventional methods for APM have involved limited analysis of 2D images when generating real-time relative motion estimates during radiotherapy treatment. Some of these methods have attempted to use 2D-to-2D or 2D-to-3D image registrations in order to estimate movement in three dimensions. However, conventional methods which rely on 2D images often suffer from one of the following limitations. First, conventional optimization-based registration methods can easily become trapped into local minima, especially if images from 2D planes are registered directly to a 3D reference dataset. Second, if a single 2D plane of acquisition is used, the through-plane motion (e.g., motion which occurs in a direction perpendicular to the 2D plane of acquisition) cannot be identified and modelled. Third, even if more than one 2D plane of acquisition is used, the information is often considered independently, leading to noisy and/or inaccurate tracking when attempting to reconcile data from the different planes.

In contrast to these technical limitations, the following APM methods and implementations provide use of a machine learning regressor model to analyze movement from 2D images captured from one or multiple planes. Specifically, a regressor model is trained to learn the relationship between features of the instantaneous 2D image(s) and the relative motion parameters—relative to a 3D reference volume. If more than one 2D plane of acquisition is used, the model can straightforwardly learn to map the multi-view information to such relative motion parameters.

The technical benefits of the following APM techniques include improved accuracy in the delivery of radiotherapy treatment dosage from a radiotherapy machine, and the evaluation of less data or user inputs to produce or perform more accurate radiotherapy machine treatment plans. Such technical benefits may result in many apparent medical treatment benefits, including improved accuracy of radiotherapy treatment, reduced exposure to unintended radiation, reduction of side-effects, more accurate compliance with a radiology treatment plan, and the like.

Figure 10:
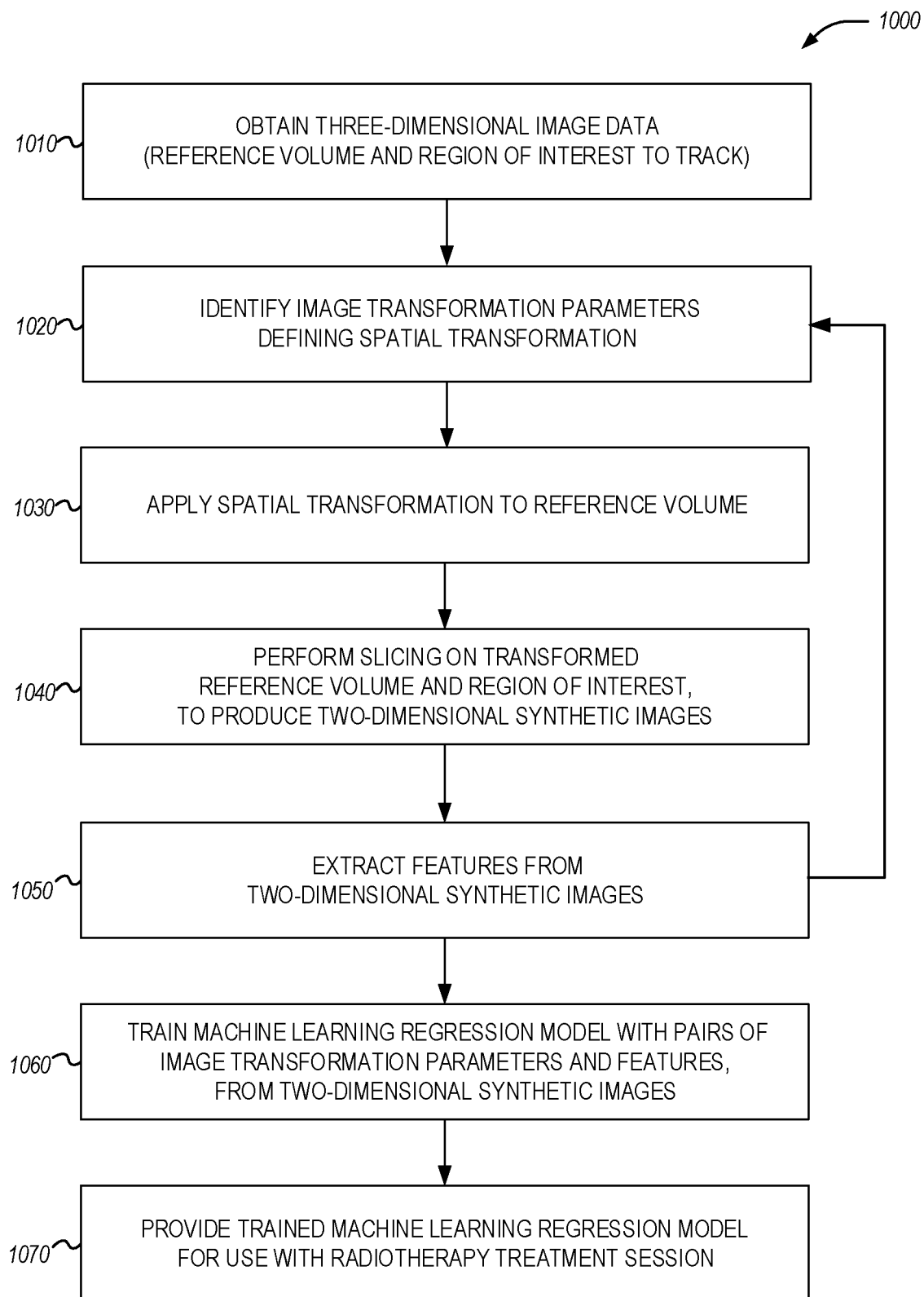
FIG. 10 illustrates a flowchart for a method of training a regression machine learning model for generating estimated motion in a region of interest, according to some examples.
Figure 11:
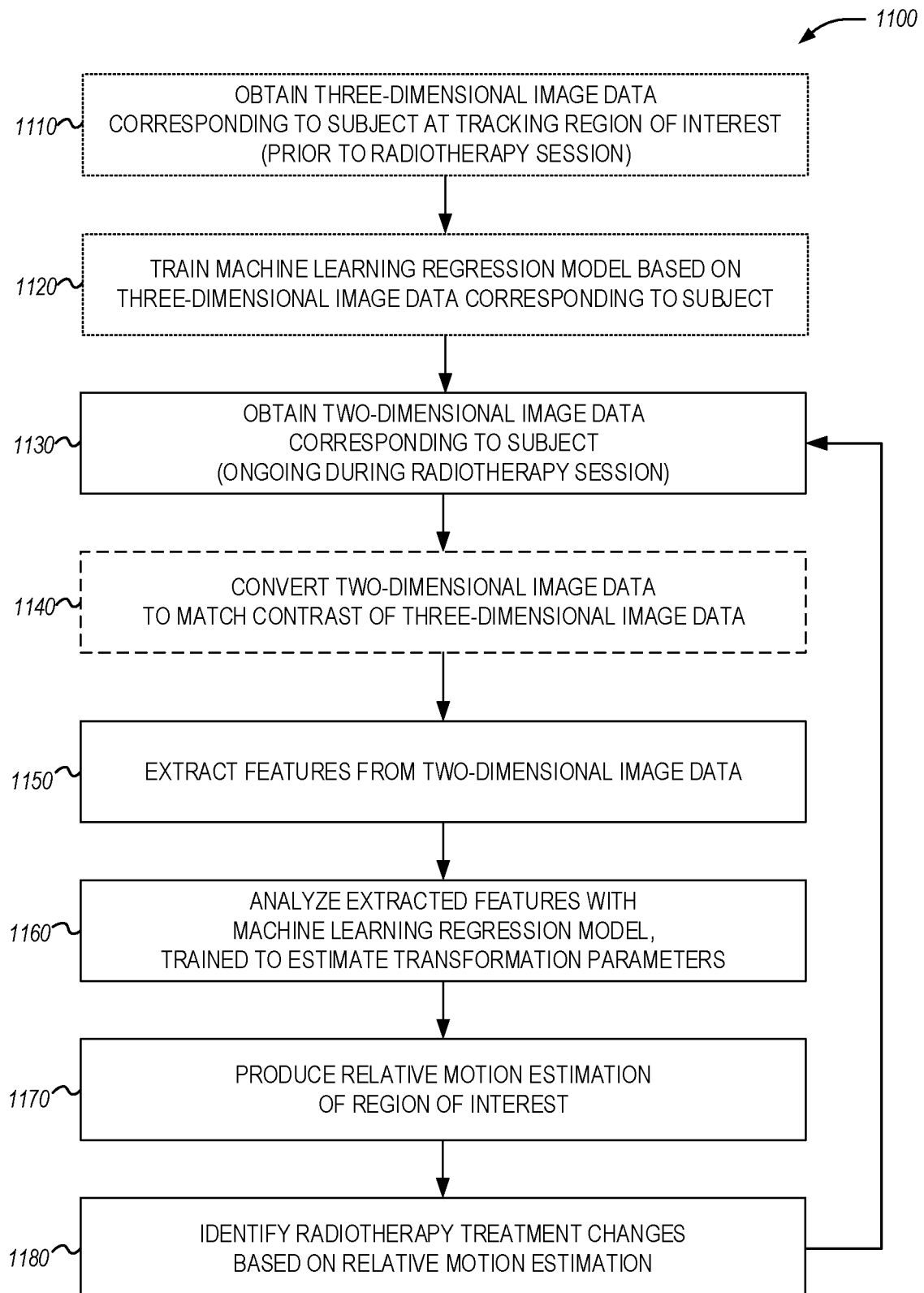
FIG. 11 illustrates a flowchart for a method of using a trained regression machine learning model for estimating movement in a region of interest, according to some examples.
Figure 12:
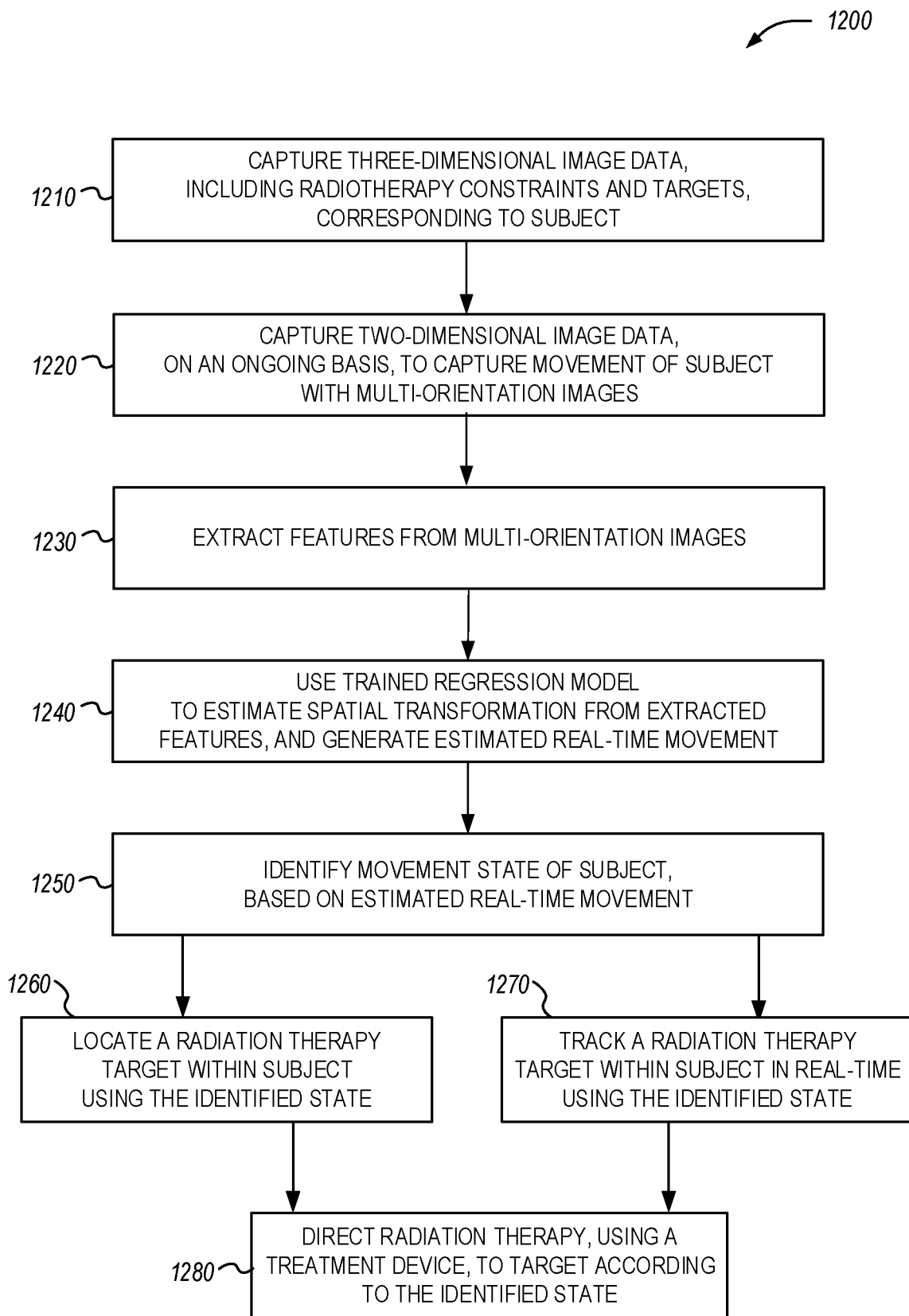
FIG. 12 illustrates a flowchart for a method performed by an image processing computing system in performing training and treatment workflows, according to some examples.
Figure 13:
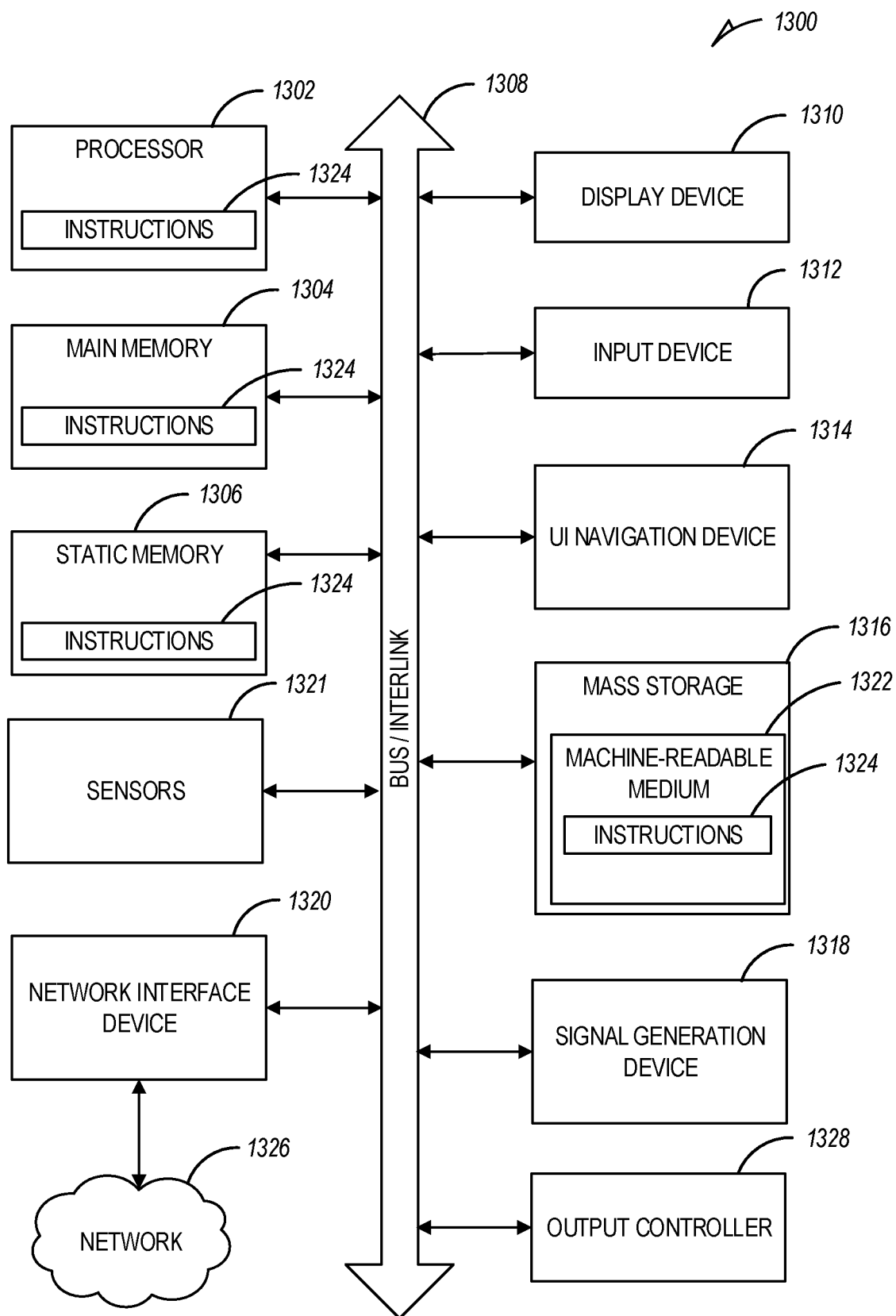
FIG. 13 illustrates an exemplary block diagram of a machine on which one or more of the methods as discussed herein can be implemented.

The following paragraphs provide an overview of example radiotherapy system implementations and treatment use cases (with reference to FIGS. 2A, 2B, and 3), including with the use of computing systems and hardware implementations (with reference to FIGS. 1 and 13). The following then continues with a discussion of a workflow using a machine learning regression model to perform APM (with reference to FIGS. 4 and 5), a workflow for training a machine learning regression model to perform APM (with reference to FIGS. 6 and 7), and processing workflows to perform APM with input data having varying image contrast (with reference to FIG. 8). Finally, a discussion of machine learning techniques (with reference to FIG. 9) is provided, along with further processing details of training and using a machine learning model, including training and use in a radiotherapy therapy session for a particular patient (FIGS. 10 to 12).

FIG. 1 illustrates a radiotherapy system 100 adapted for using machine learning models for assisting anatomic position monitoring. The anatomic position monitoring may be used to determine a patient state to enable the radiotherapy system 100 to provide radiation therapy to a patient based on specific aspects of captured medical imaging data. The radiotherapy system includes an image processing computing system 110 which hosts patient state processing logic 120. The image processing computing system 110 may be connected to a network (not shown), and such network may be connected to the Internet. For instance, a network can connect the image processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170, and a treatment device 180 (e.g., a radiation therapy device). As an example, the image processing computing system 110 can be configured to perform image patient state operations by executing instructions or data from the patient state processing logic 120, as part of operations to generate and customize radiation therapy treatment plans to be used by the treatment device 180.

The image processing computing system 110 may include processing circuitry 112, memory 114, a storage device 116, and other hardware and software-operable features such as a user interface 140, communication interface, and the like. The storage device 116 may store computer-executable instructions, such as an operating system, radiation therapy treatment plans (e.g., original treatment plans, adapted treatment plans, or the like), software programs (e.g., radiotherapy treatment plan software, artificial intelligence implementations such as machine learning models, deep learning models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™ FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the patient state processing logic 120 and the user interface 140). The instructions may also reside, completely or at least partially, within the memory 114 and/or within the processing circuitry 112 during execution thereof by the image processing computing system 110, with the memory 114 and the processing circuitry 112 also constituting machine-readable media.

The memory 114 or the storage device 116 may constitute a non-transitory computer-readable medium. For example, the memory 114 or the storage device 116 may store or load instructions for one or more software applications on the computer-readable medium. Software applications stored or loaded with the memory 114 or the storage device 116 may include, for example, an operating system for common computer systems as well as for software-controlled devices. The image processing computing system 110 may also operate a variety of software programs comprising software code for implementing the patient state processing logic 120 and the user interface 140. Further, the memory 114 and the storage device 116 may store or load an entire software application, part of a software application, or code or data that is associated with a software application, which is executable by the processing circuitry 112. In a further example, the memory 114 or the storage device 116 may store, load, or manipulate one or more radiation therapy treatment plans, imaging data, patient state data, dictionary entries, artificial intelligence model data, labels, and mapping data, etc. It is contemplated that software programs may be stored not only on the storage device 116 and the memory 114 but also on a removable computer medium, such as a hard drive, a computer disk, a CD-ROM, a DVD, a HD-DVD, a Blu-Ray DVD, USB flash drive, a SD card, a memory stick, or any other suitable medium; such software programs may also be communicated or received over a network.

Although not depicted, the image processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber optic, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the image processing computing system 110 may obtain image data 160 from the image data source 150, for hosting on the storage device 116 and the memory 114. In an example, the software programs operating on the image processing computing system 110 may convert or transform medical images of one format (e.g., MRI) to another format (e.g., CT), such as by producing synthetic images, such as a pseudo-CT image. In another example, the software programs may register or associate a patient medical image (e.g., a CT image or an MR image) with that patient's dose distribution of radiotherapy treatment (e.g., also represented as an image) so that corresponding image voxels and dose voxels are appropriately associated. In another example, the software programs may visualize, hide, emphasize, or de-emphasize some aspect of anatomical features, patient measurements, patient state information, or dose or treatment information, within medical images. The storage device 116 and memory 114 may store and host data to perform these purposes, including the image data 160, patient data, and other data required to create and implement a radiation therapy treatment plan and associated patient state estimation operations.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 160 to be received or obtained in memory 114, and processed using the patient state processing logic 120. For example, the image processing computing system 110 may receive image data 160 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing/simulation environment that uses a network to collaboratively perform the embodiments described herein (such as in an edge computing environment). In addition, such network may be connected to the Internet to communicate with servers and clients that reside remotely on the Internet.

In further examples, the processing circuitry 112 may utilize software programs (e.g., a treatment planning software) along with the image data 160 and other patient data to create a radiation therapy treatment plan. In an example, the image data 160 may include 2D or 3D volume imaging, such as from a CT or MR. In addition, the processing circuitry 112 may utilize aspects of AI such as machine learning, deep learning, and neural networks to generate or control various aspects of the treatment plan, including in response to an estimated patient state or patient movement as discussed in the following examples.

For instance, such software programs may utilize patient state processing logic 120 to implement a patient state determination workflow 130, using the techniques further discussed herein. The processing circuitry 112 may subsequently then modify and transmit the executable radiation therapy treatment plan via a communication interface and the network to the treatment device 180, where the radiation therapy plan will be used to treat a patient with radiation via the treatment device, consistent with results of the patient state determination workflow 130. Other outputs and uses of the software programs and the patient state determination workflow 130 may occur with use of the image processing computing system 110. As discussed further below, the processing circuitry 112 may execute a software program that invokes the patient state processing logic 120 to implement functions including aspects of image processing and registration, feature extraction, machine learning model processing, and the like.

In an example, the image data 160 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 160 may also include or be associated with auxiliary information, such as segmentations/contoured images, or dose images. In an example, the image data 160 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MM imaging device, or other medical imaging devices for obtaining the medical images of the patient. The image data 160 may be received and stored in any type of data or any type of format (e.g., in a Digital Imaging and Communications in Medicine (DICOM) format) that the image acquisition device 170 and the image processing computing system 110 may use to perform operations consistent with the disclosed embodiments.

In an example, the image acquisition device 170 may be integrated with the treatment device 180 as a single apparatus (e.g., an MRI device combined with a linear accelerator, also referred to as an "MR-LINAC", as shown and described in FIG. 3 below). Such an MR-LINAC can be used, for example, to precisely determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The image processing computing system 110 may communicate with an external database through a network to send/receive a plurality of various types of data related to image processing and radiotherapy operations. For example, an external database may include machine data that is information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MM pulse sequence, and the like. The external database may be a storage device and may be equipped with appropriate database administration software programs. Further, such databases or data sources may include a plurality of devices or systems located either in a central or a distributed manner.

The image processing computing system 110 can collect and obtain data, and communicate with other systems, via a network using one or more communication interfaces, which are communicatively coupled to the processing circuitry 112 and the memory 114. For instance, a communication interface may provide communication connections between the image processing computing system 110 and radiotherapy system components (e.g., permitting the exchange of data with external devices). For instance, the communication interface may in some examples have appropriate interfacing circuitry from an output device 142 or an input device 144 to connect to the user interface 140, which may be a hardware keyboard, a keypad, or a touch screen through which a user may input information into the radiotherapy system 100.

As an example, the output device 142 may include a display device which outputs a representation of the user interface 140 and one or more aspects, visualizations, or representations of the medical images. The output device 142 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D volume), or any related information to the user. The input device 144 connected to the user interface 140 may be a keyboard, a keypad, a touch screen or any type of device that a user may input information to the radiotherapy system 100. Alternatively, the output device 142, the input device 144, and features of the user interface 140 may be integrated into a single device such as a smartphone or tablet computer, e.g., Apple iPad®, Lenovo Thinkpad®, Samsung Galaxy®, etc.

Furthermore, many components of the radiotherapy system 100 may be implemented with a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the image processing computing system 110, the image data sources 150, or like components, may be implemented as a virtual machine or within a cloud-based virtualization environment.

The patient state processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 160 obtained from one or more patients via the image acquisition device 170, including in real-time settings, defined further below. The image data source 150 or other databases may also store data to be used by the patient state processing logic 120 when executing a software program that performs patient state estimation operations, or when creating, monitoring, or modifying radiation therapy treatment plans. Further, various databases may store machine learning or other AI models, including the algorithm parameters, weights, or other data constituting the model learned by the network and the resulting predicted or estimated data. The image processing computing system 110 thus may obtain and/or receive the image data 160 (e.g., 2D MRI slice images, CT images, 2D Fluoroscopy images, X-ray images, 3D MRI images, 4D MRI images, etc.) from the image data source 150, the image acquisition device 170, the treatment device 180 (e.g., a MR-LINAC), or other information systems, in connection with performing image patient state estimation as part of treatment or diagnostic operations.

The image acquisition device 170 can be configured to acquire one or more images of the patient's anatomy relevant to a region of interest (e.g., a target organ, a target tumor or both). Each image, typically a 2D image or slice, can include one or more parameters (e.g., a 2D slice thickness, an orientation, an origin and field of view, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "real-time" while a patient is undergoing radiation therapy treatment, for example, when using the treatment device 180 (with "real-time" meaning, in an example, acquiring the data in 10 milliseconds or less). In another example for some applications, real-time may include a timeframe within (e.g., up to) 300 milliseconds. In an example, real-time may include a time period fast enough for a clinical problem being solved by techniques described herein. In this example, real-time may vary depending on target speed, radiotherapy margins, lag, response time of a treatment device, etc.

The patient state processing logic 120 in the image processing computing system 110 is depicted as implementing a patient state determination workflow 130 with various aspects of monitoring and estimation of a patient state provided by models or algorithms. In an example, the patient state determination workflow 130 uses a real-time image input stream 132 (e.g., 2D partial measurements, such as from a CT or MR), which is analyzed by anatomic position monitoring 136 functions to estimate a patient state. In a further example, the patient state determination workflow 130 uses a real-time sensor data stream 134 (e.g., breathing belt measurements, other external, non-image sensor measurements) which is analyzed by anatomic position monitoring 136 functions to estimate or refine the patient state.

The patient state determination workflow 130 further involves aspects of anatomic position monitoring 136, such as determined within the trained regression model discussed in further examples below. The data provided from anatomic position monitoring 136 may be used for producing or controlling a patient state estimation 138. The patient state estimation 138 may produce data that is used to control the treatment device 180 or other aspects of the radiotherapy session.

Figure 2A:
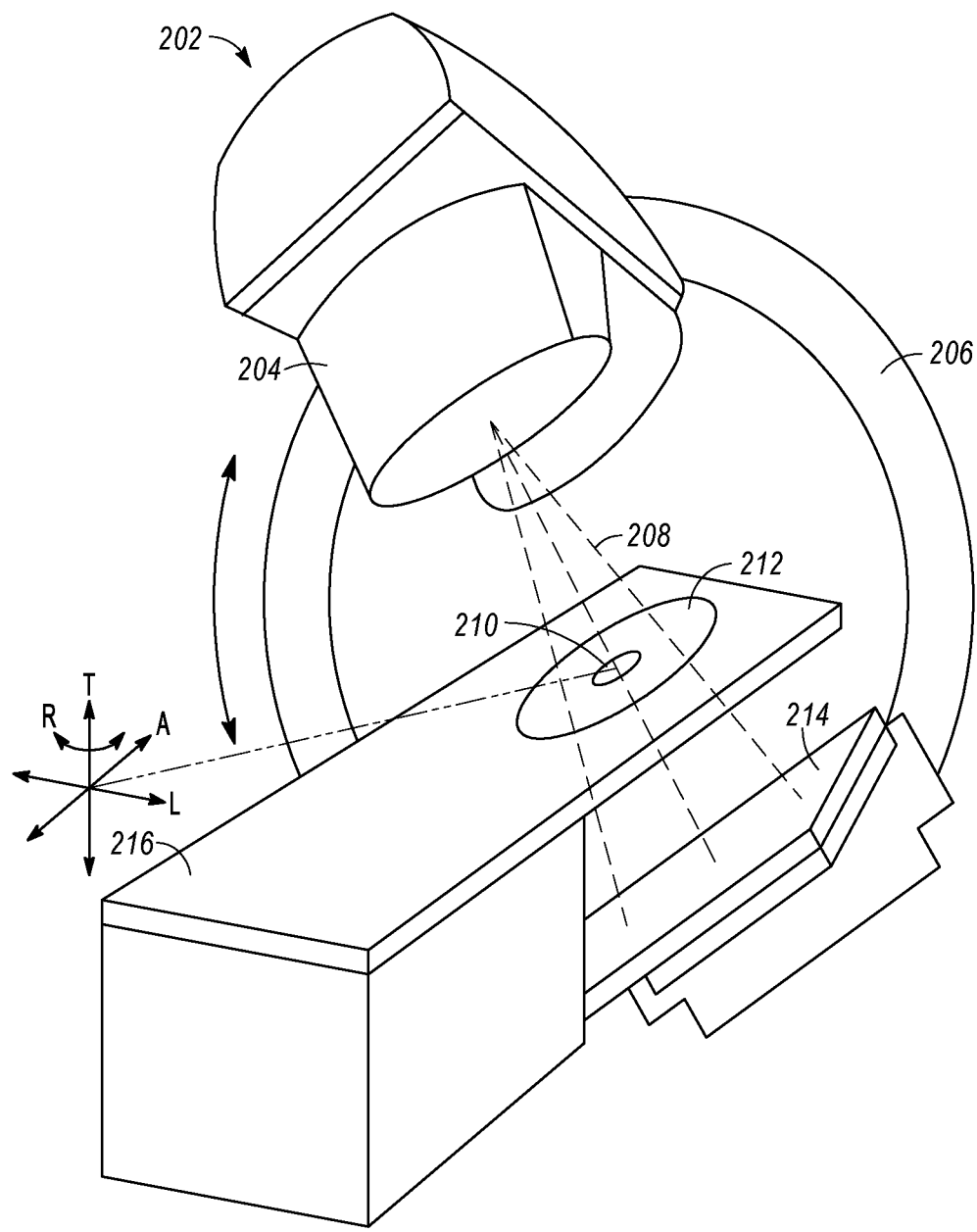
FIG. 2A illustrates a radiation therapy system having radiation therapy output configured to provide a therapy beam, according to some examples.

FIG. 2A illustrates a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC. A MLC may be used for shaping, directing, or modulating an intensity of a radiation therapy beam to the specified target locus within the patient. The leaves of the MLC, for instance, can be automatically positioned to define an aperture approximating a tumor cross-section or projection, and cause modulation of the radiation therapy beam. For example, the leaves can include metallic plates, such as comprising tungsten, with a long axis of the plates oriented parallel to a beam direction and having ends oriented orthogonally to the beam direction. Further, a "state" of the MLC can be adjusted adaptively during a course of radiation therapy treatment, such as to establish a therapy beam that better approximates a shape or location of the tumor or other target locus.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor precisely. The MLC may be integrated and included within gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an example, the imaging detector 214 can be located within a field of the radiation beam 208.

The imaging detector 214 can be mounted on the gantry 206 (preferably opposite the radiation therapy output 204), such as to maintain alignment with the radiation beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation beam 208 or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
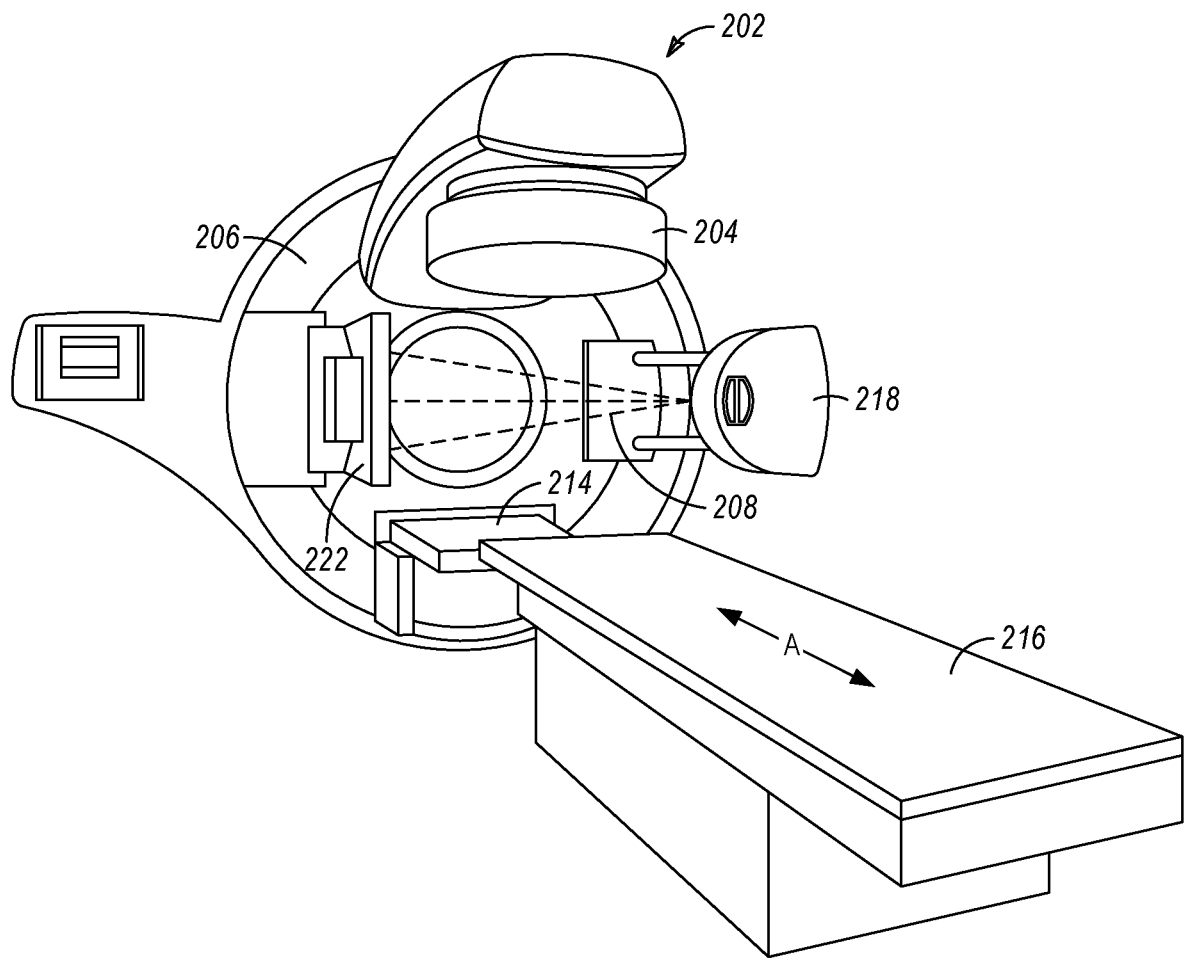
FIG. 2B illustrates a system including a combined radiation therapy system and an imaging system, such as a cone beam computed tomography (CBCT) imaging system, according to some examples.

FIG. 2B illustrates a radiation therapy device 202 that may include a combined LINAC and an imaging system, such as a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical radiation beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative example of FIG. 2B, the radiation therapy output 204 and the X-ray source 218 can be mounted on the same rotating gantry 206, rotationally separated from each other by 90 degrees. In another example, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
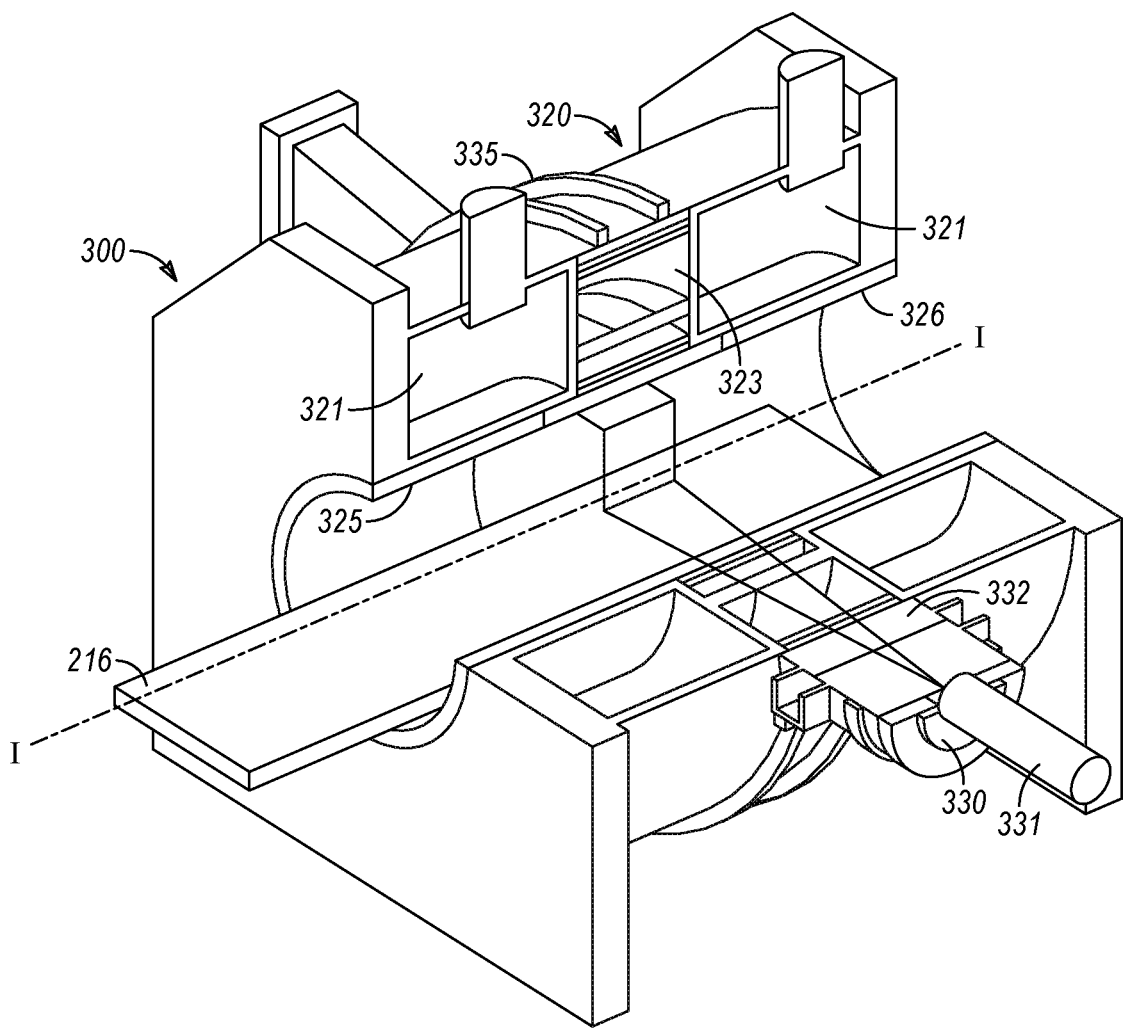
FIG. 3 illustrates a partially cut-away view of a system including a combined radiation therapy system and an imaging system, such as a nuclear magnetic resonance (MR) imaging (MRI) system, according to some examples.

FIG. 3 depicts a radiation therapy system 300 that can include combining a radiation therapy device 202 and an imaging system, such as a magnetic resonance (MR) imaging system (e.g., known in the art as an MR-LINAC) consistent with the disclosed examples. As shown, system 300 may include a couch 216, an image acquisition device 320, and a radiation delivery device 330. System 300 delivers radiation therapy to a patient in accordance with a radiotherapy treatment plan. In some examples, image acquisition device 320 may correspond to image acquisition device 170 in FIG. 1 that may acquire origin images of a first modality (e.g., an MRI image) or destination images of a second modality (e.g., an CT image).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some examples, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some examples, the one or more coils in magnet 321 may be spaced such that a central window 323 of magnet 321 is free of coils. In other examples, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiation delivery device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In examples where magnet 321 can also include a central window 323 between coils, the two windows may be aligned with each other.

In some examples, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain examples and is not intended to be limiting.

Radiation delivery device 330 may include the radiation source 331, such as an X-ray source or a LINAC, and an MLC 332. Radiation delivery device 330 may be mounted on a chassis 335. One or more chassis motors (not shown) may rotate the chassis 335 around the couch 216 when the couch 216 is inserted into the treatment area. In an example, the chassis 335 may be continuously rotatable around the couch 216, when the couch 216 is inserted into the treatment area. Chassis 335 may also have an attached radiation detector (not shown), preferably located opposite to radiation source 331 and with the rotational axis of the chassis 335 positioned between the radiation source 331 and the detector. Further, the device 330 may include control circuitry (not shown) used to control, for example, one or more of the couch 216, image acquisition device 320, and radiotherapy device 330. The control circuitry of the radiation delivery device 330 may be integrated within the system 300 or remote from it.

During a radiotherapy treatment session, a patient may be positioned on couch 216. System 300 may then move couch 216 into the treatment area defined by the magnet 321, coils 325, 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 generally illustrate examples of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

As noted above, when performing radiation therapy, underlying 3D patient motion must be estimated and tracked in order to accurately deliver radiation therapy treatment at a correct location. To do this, radiotherapy treatment techniques involve an estimation of the relative motion of a specific object contained in a specified region of interest, relative to a reference volume which contains auxiliary information such as contoured regions of interest or the dose plan. This estimation and monitoring of a location for a specific object is referred to herein as anatomic position monitoring (APM).

Figure 4:
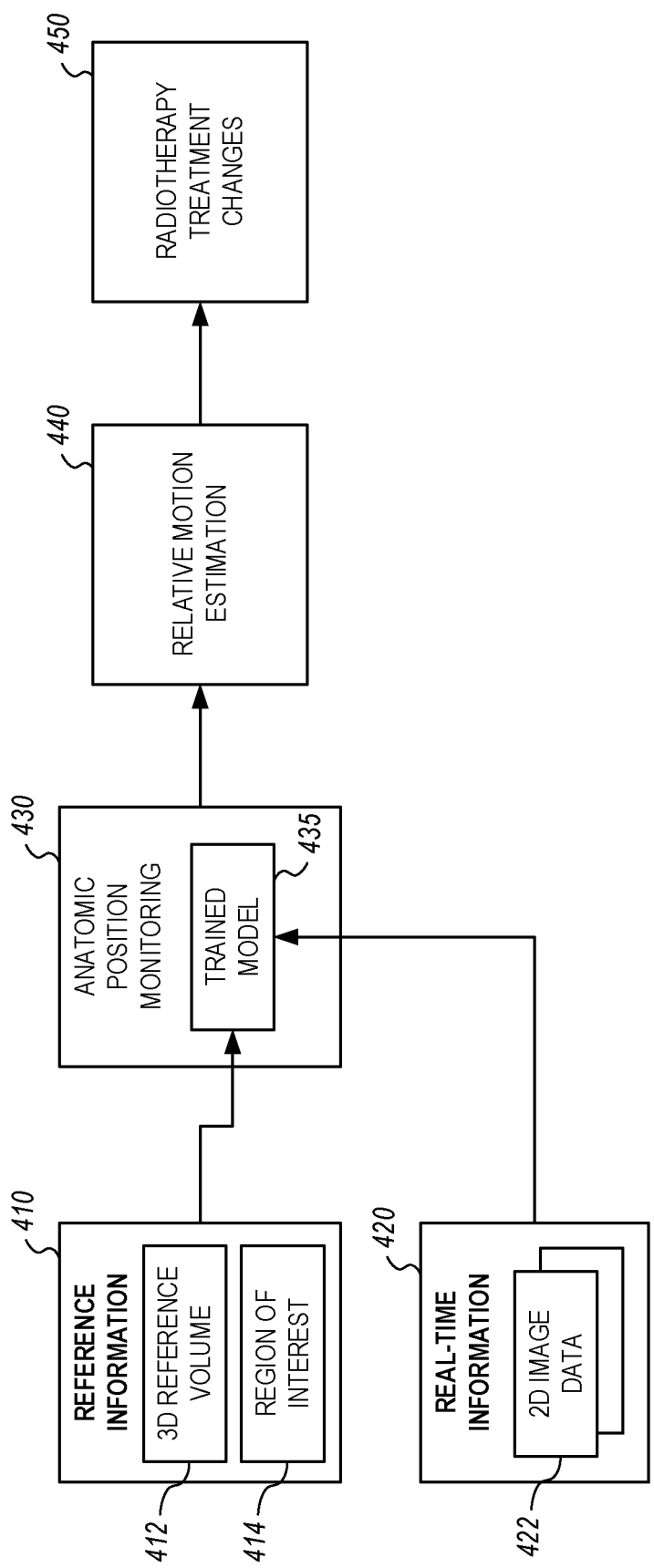
FIG. 4 illustrates anatomic position monitoring operations, according to some examples.

FIG. 4 provides a high-level view of APM operations. The goal of APM is to produce a real-time motion estimation 440 of an object contained in a region of interest, relative to its position in a known 3D reference space. The relative motion estimation 440 then can be used to adjust the radiotherapy treatment and cause radiotherapy treatment changes 450 that are directed to one or more regions of interest within the 3D reference space. It will be understood that a variety of techniques for adjusting or modifying the location, type, amount, or characteristics of radiotherapy treatment based on motion may be utilized, based upon the identification of the anatomic position and an estimate of relative motion.

The operations in FIG. 4, in more detail, illustrate how reference information 410 for a human subject may be correlated to movement changes that are identified from real-time information 420 for the human subject. The reference information 410 may include imaging data from a 3D reference volume 412 (e.g., produced from an MRI or CT scan), and a definition of a region of interest 414 (e.g., a mask or area defining a target organ, a target tumor or both). The real-time information 420 may include 2D imaging data 422 (e.g., produced from 2D MR images or kV projection imaging), collected over time from a single or multiple orientations (e.g., a first image captured at a coronal plane, and a second image captured at a sagittal plane). Other forms of real-time information 420, not depicted, may include position monitoring signals (e.g., a signal from a breathing belt, sensor data, etc.) captured from observed patient body movement.

Based on input data of the 3D reference volume 412, an accompanying tracking region of interest 414, and real-time information 420 (e.g., instantaneous, ongoing) relating to the patient (e.g., 2D imaging data 422 captured on an ongoing basis), an APM algorithm 430 analyzes the real-time information 420 to determine movement relative to the reference information 410. The APM algorithm 430 may be provided by a trained machine learning model 435, such as a trained regression model or other artificial intelligence algorithm implementation, which estimates motion in a 3D space based on analysis of the real-time information 410.

In an example, the APM algorithm 430 uses the trained model 435 to generate a relative motion estimation 440 in the form of transformation parameters that describe the motion of the tracked region relative to the reference volume 412. The relative motion estimation 440 may be processed to produce radiotherapy treatment changes 450 that dynamically gate the radiotherapy beam (e.g., turn the beam on or off in real-time), or dynamically effect a change in direction, shape, position, intensity, amount, or type of a beam in the radiotherapy treatment. As a simple example, radiotherapy treatment changes 450 may include control of a radiotherapy beam, such as starting or stopping radiotherapy treatment output, or turning a radiotherapy beam on or off, based on movement caused by patient breathing.

The following paragraphs provide examples of a treatment workflow adapted for performing APM 430 with use of the trained model 435, including a specific example of a regression model which can analyze individual 2D images captured in real-time during a radiotherapy treatment session. The following paragraphs also provide examples of a training workflow adapted for developing the trained model 435. It will be understood that the following treatment workflow process may be performed and repeated many times (e.g., on an ongoing, real-time basis, to monitor for patient movement) as part of a radiotherapy treatment session for a single patient. It will also be understood that the following training workflow process may be performed a single time or multiple times (e.g., a single time in an offline training setting, although the training workflow may be modified for online training as additional reference information is obtained). The following training and treatment workflows may also be adapted for use of multiple treatment sessions for a particular patient, or for multiple patients.

Figure 5:
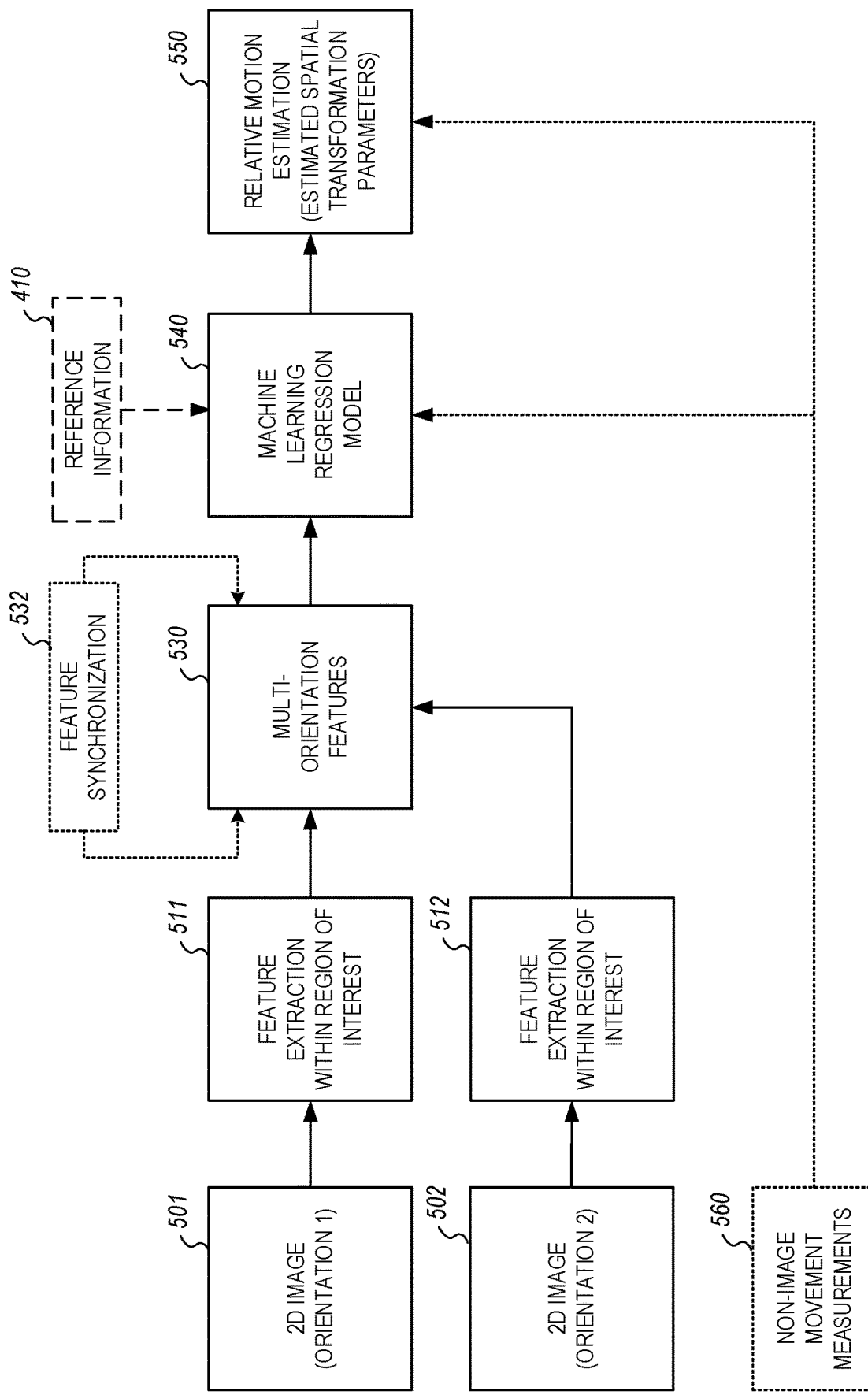
FIG. 5 illustrates a treatment workflow for performing anatomic position monitoring, using results of a trained machine learning regression model, according to some examples.

FIG. 5 provides a high-level illustration of a treatment workflow for performing APM 430, using results of a trained machine learning regression model 540. This treatment workflow includes the capture and processing of real-time data in the form of multiple real-time 2D images, feature extraction from the multiple real-time 2D images, and analysis of the extracted features with the machine learning regression model 540. The machine learning regression model 540 is trained to produce a data output, in the form of spatial transformation parameters which describe relative motion estimation 550.

In the example of FIG. 5, the real-time data includes 2D images captured in real-time from a patient, using two different planes of acquisition (2D image 501 captured at a first orientation or plane, and 2D image 502 captured at a second orientation or plane). Using these two 2D images of respective orientations, feature extraction is performed on each image independently, including feature extraction operations 511 within the region of interest performed on the first orientation image and feature extraction operations 512 within the region of interest performed on the second orientation image. Although images from multiple planes of acquisition are illustrated in this example, it will be understood that the techniques are also applicable to one or more images obtained from one plane of acquisition, or one or more images obtained from more than two planes of acquisition.

In the following discussed examples, reference is made to a scenario where the real-time image measurements are provided from a 2D MR imaging modality, which is used to obtain instantaneous 2D images from two different planes of acquisition (e.g., orthogonal sagittal and coronal planes) continuously throughout treatment. In another example, kV projection imaging may be used instead of MR imaging to obtain instantaneous 2D images. Still other forms of instantaneous, non-image movement measurements 560 (partial measurements), such as a signal from a breathing belt or body sensor, may also be used instead of some image measurements, or in combination with image-based measurements. Thus, it will be understood that the presently described treatment and training methods are not limited to use of 2D MR images.

As shown, the real-time acquired 2D images 501, 502—each acquired from a different plane of acquisition, such as from coronal and sagittal planes—is followed by separate instances of feature extraction. Such feature extraction is performed on each image independently with extraction operations 511, 512. Feature extraction may involve performing image processing steps (not shown in FIG. 5), such as deformable image registration, and may additionally be followed by dimensionality reduction techniques (such as principal component analysis) for algorithmic and/or computational efficiency (e.g., to reduce the number of features before regression analysis). In an example using kV projection imaging as the input 2D images 501, 502, fiducial positions could be extracted and used as features. In addition, feature extraction may be performed within and/or extracted from a limited region of interest (ROI) provided alongside the 3D reference volume. Other types of feature identification and extraction may be used.

Following feature extraction (extraction operations 511, 512) on each 2D image (images 501, 502), the extracted features are concatenated or combined into multi-orientation features 530 (e.g., a multi-dimensional vector, representing features in multiple orientations). The machine learning regression model 540 then analyzes the multi-orientation features 530 as input, to estimate the motion relative to some reference (e.g., relative to 3D reference volume of the patient, provided in reference information 410 used to train the model 540). The output of the machine learning regression model 540 may include estimated spatial transformation parameters which represent relative motion estimation 550 (relative to the anatomy depicted in the 3D reference volume, indicating motion provided from translation and/or rotation in the three dimensions).

In further examples, the workflow referenced within FIG. 5 can be performed independently for different structures, using different regions of interest for the tumors and/or organs at risk. Thus, in some examples, different features may be extracted for different anatomical structures; likewise, different trained regression models may be trained and used to analyze motion of different anatomical structures.

In practice, 2D images with different planes of acquisition may be acquired sequentially and not in parallel at the same time, which may result in relative shifts in the observed anatomy between the 2D images acquired in different planes. With sequential rather than parallel acquisition, the discrepancy may be ignored if the discrepancy is sufficiently small. In other examples, only the most recent 2D image may be used, or suitable prediction algorithms can be used to synchronize (in time) the content of multiple 2D feature vectors. For example, feature synchronization 532 may be applied using a long short-term memory (LS™) model, to forecast the features describing the contents of one imaging plane such that it coincides with features of the other imaging plane (e.g., obtained 200 ms later). Such feature synchronization 532 may yield a synchronized multi-orientation feature vector that is used in the set of multi-orientation features 530 and provided as input to the model 540.

Figure 6:
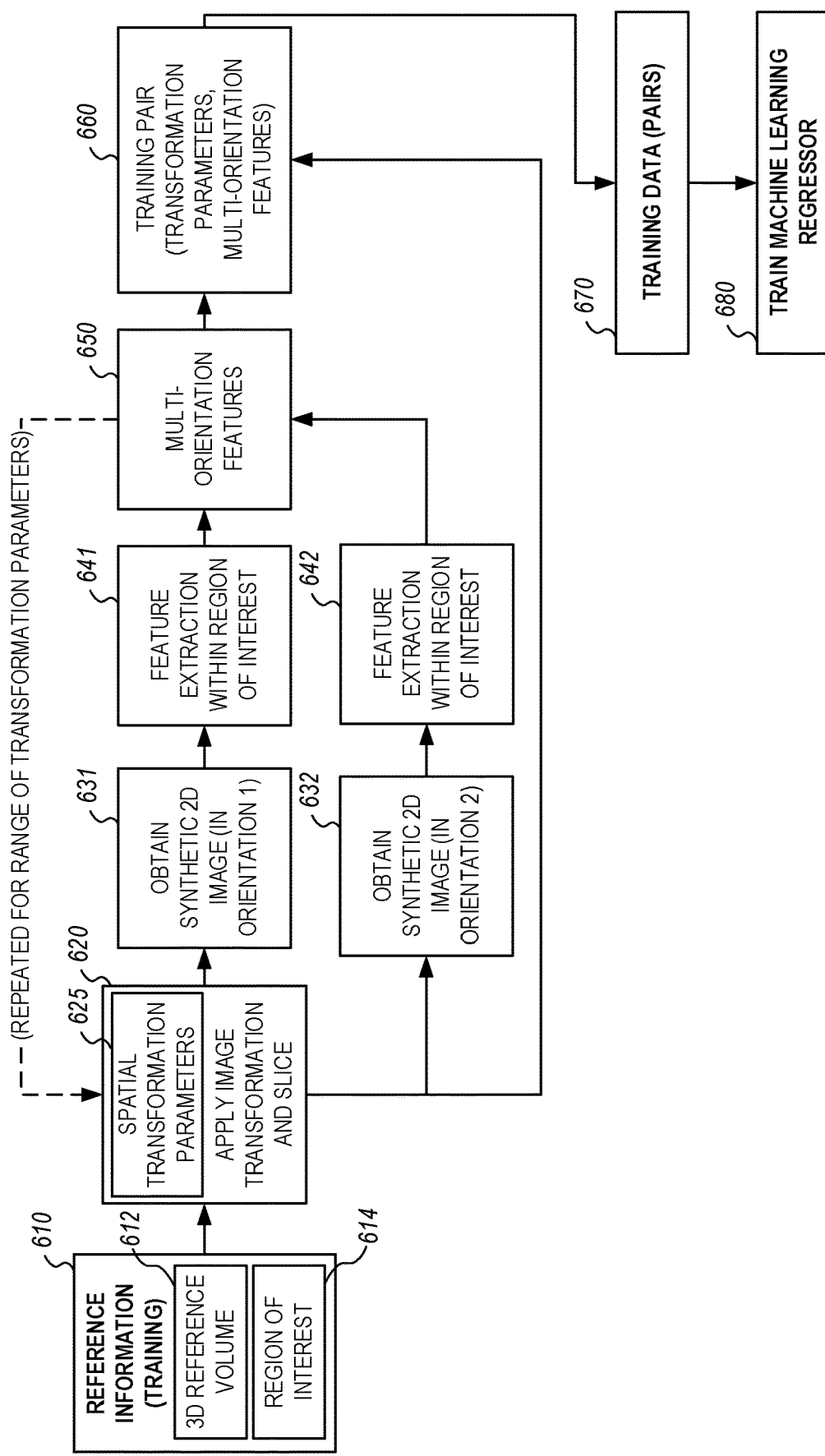
FIG. 6 illustrates a training workflow for an anatomic position monitoring algorithm, implemented with a machine learning regression model, according to some examples.

FIG. 6 provides a high-level overview of an example training workflow for the APM algorithm 430, implemented with a machine learning regression model. Within FIG. 6, the generation of a training data pair 660 is depicted for a particular image transformation, which is repeated for a range of image transformations to produce a training data set 670. In an example, a training data pair 660 includes (1) a known set of spatial transformation parameters 625 (defining a transformation 620 applied to reference information 610 including a reference volume 612 and region of interest 614), and (2) a set of multi-orientation features 650 summarizing the joint appearance of the patient anatomy as observed from the two 2D images 631, 632 given the known set of spatial transformation parameters 625. This process is repeated to obtain the training data set 670 (a collection of training pairs), from which a machine learning regressor will be trained with a training process 680. This training process 680 enables the model to analyze a multi-orientation feature set (as model input) and generate a corresponding motion parameter set (as model output).

To generate a respective training pair 660, image data in the 3D reference volume 612 (e.g., image data which includes and designates the region of interest 614) is first transformed with a specified set of transformation parameters 625. The image data is then resampled to the particular specifications of each plane of 2D image acquisition ("sliced"), yielding two 2D images 631, 632 in different orientations. Features are then independently extracted 641, 642 from each of the two 2D images 631, 632, and are combined to form a joint representation of both views. This is repeated by sampling over a range of transformation parameters, generating a training data set 670 providing a plurality of training pairs for various types of transformations. This range of transformation parameters may be determined heuristically, or informed by a prior set of examples on similar radiotherapy treatment cases. From this training data set 670, the training process 680 applied to a machine learning regressor can be performed to map input multi-orientation feature sets to their corresponding output motion parameters.

The training workflow depicted in FIG. 6 is compatible with a range of different motion parameterizations. For example, a particular instance of motion may be parameterized by a particular translation vector, a rigid or affine transformation, or even a full deformation vector field. The training workflow is also compatible with a wide range of choices concerning the particular machine learning algorithm used for regression (e.g., both linear and non-linear models).

In an example, the local motion of the tracked structure is characterized using a 3D translation vector (e.g., providing the x-, y- and z-components of the translation relative to the 3D reference volume 612). For feature extraction, for each slice orientation independently (e.g., feature extraction operations 641, 642), the 2D image is deformably registered to a common 2D target image, followed by principal component analysis (PCA) on the resultant 2D deformation vector field (DVF) within the provided in-plane 2D region of interest to extract a minimal set of informative features. The 2D target images (e.g., images 631, 632), which serve as the target images for each slice orientation during 2D deformable registration, can be obtained by slicing the 3D reference volume 612 using the specifications of each imaging plane of acquisition. In a further example, two PCA models may be used, one per imaging plane of acquisition. Each of the PCA models maps DVFs extracted from the respective in-plane ROIs to a minimal set of informative features, and can be trained on the sets of DVFs produced during the training phase. Feature extraction using this approach is discussed further below.

Figure 7:
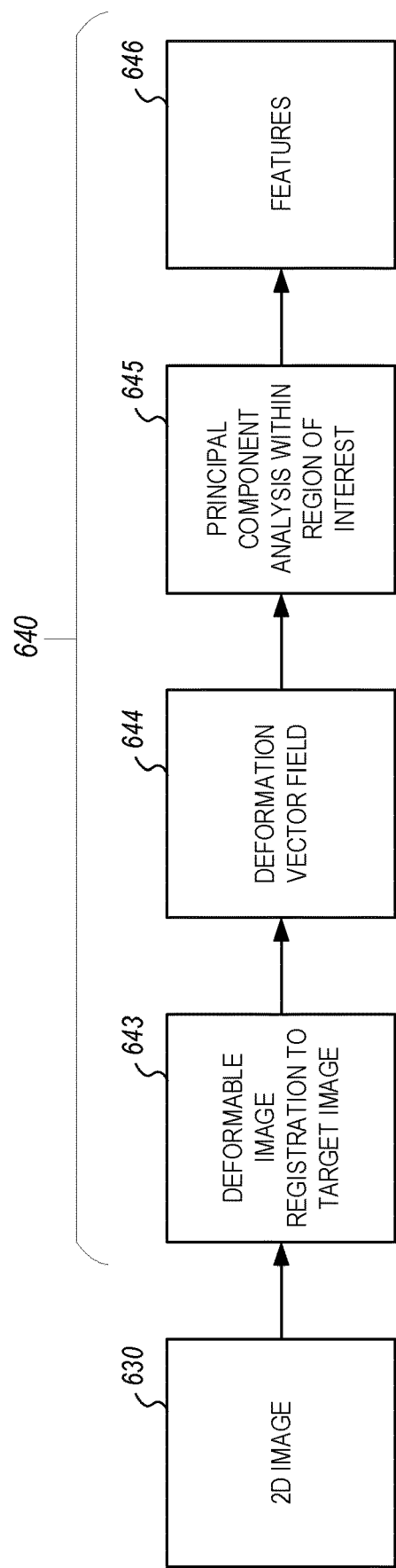
FIG. 7 illustrates feature extraction using deformable registration and principal component analysis, according to some examples.

FIG. 7 depicts additional detail of feature extraction using deformable registration and principal component analysis (operation 640 corresponding to operations 641, 642 depicted in FIG. 6). Given an input 2D image 630, the 2D image 630 is deformably registered 643 to its corresponding 2D target image (e.g., registered to an image in the same imaging plane of acquisition). The resulting deformation vector field 644 within the in-plane 2D region of interest is extracted and reduced in dimensionality using PCA 645, yielding a minimal set of informative features 646.

In further examples, the present technique may be adapted to support differences in image contrast between the reference volume and the real-time images. As will be understood, the 3D reference volume that is obtained at the time of radiotherapy treatment may be acquired using any one of a multitude of MR pulse acquisition sequences, e.g., T1-weighted, T2-weighted, proton density or contrast-agent enhanced images, depending on the specific clinical requirements. On the other hand, there may be considerably less flexibility concerning the choice of a necessarily fast pulse sequence used to acquire the instantaneous 2D images throughout treatment. In such cases, the set of 2D images used for training (e.g. obtained by slicing the 3D reference volume) may have different characteristics compared to the instantaneous 2D images acquired throughout treatment, and a naïve application of the treatment workflow (e.g., portrayed in FIG. 5) may result in poor tracking.

To accommodate images using different types of contrast, one of the following approaches may be applied.

In a first approach, robust contrast-invariant registration algorithms can be used for feature extraction (e.g., feature extraction operations 640, 641, 642 as discussed within FIGS. 6 and 7. This ensures that the deformation vector fields computed for feature extraction during the training workflow (in which registration is between same-contrast images) are qualitatively similar to those computed during the treatment workflow (in which registration may be between different-contrast images). However, developing an accurate real-time implementation of contrast-invariant deformable registration technique can be challenging and may be beyond the technical limitations of some image processing approaches. For this reason, the next two approaches listed below avoid such a requirement.

In a second approach, an intermediate 3D reference volume, with the same contrast as the instantaneous 2D images, can be acquired. This intermediate reference volume can then be registered to the primary 3D reference volume (either automatically using a registration algorithm of choice, or with user guidance), and subsequently used in the training and test workflows. The acquisition of such an intermediate 3D reference volume may increase the pre-treatment setup time, limiting clinical efficiency.

In a third approach, a preparation step that includes the acquisition of instantaneous 2D images can be used to create 2D template images with the same contrast as those acquired during the test-time workflow. In this approach, standard mono-contrast deformable registration can be used for feature extraction. Such 2D templates may be created using a variety of template-building approaches.

Due to possible patient motion between the time of acquisition of the 3D reference volume and that of the pre-treatment set of instantaneous 2D images, there may be an offset between the two sets of images that must be accounted for. To this end, the primary 3D reference volume can be registered (either automatically using a registration algorithm of choice, or with user guidance) to the two 2D templates, yielding an offset and an updated 3D reference volume and ROI (as discussed below with reference to FIG. 8). Then, during the training workflow, the updated 3D reference volume and ROI can be used. During the treatment workflow, the same-contrast 2D templates can be used as the registration targets for feature extraction. Finally, the concatenation of the previously estimated offset with the relative motion estimates (i.e. the output of the machine learning regressor) yields the desired motion estimates, i.e. relative to the primary (non-updated) reference volume.

Figure 8:
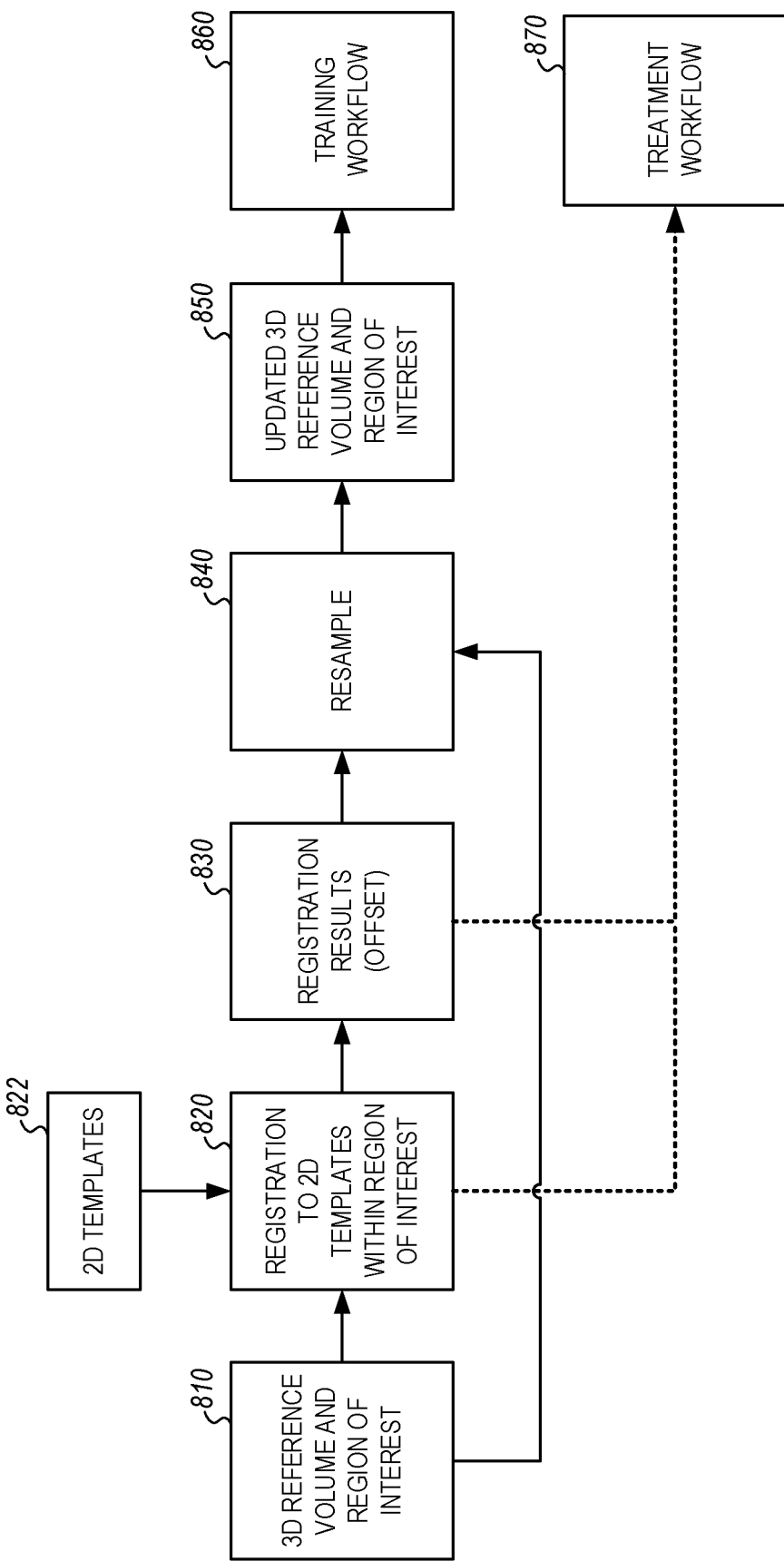
FIG. 8 illustrates a corrective procedure using registration for feature extraction, to account for offsets due to different contrast images, according to some examples.

FIG. 8 depicts a corrective procedure using registration for feature extraction, to account for possible offsets between the 3D reference volume 810 and 2D templates 822 having the same contrast. The 3D reference volume 810 is (automatically or with user guidance) registered 820 to the two same-contrast 2D templates, yielding an offset 830 that is resampled 840 into an updated 3D reference volume 850. The updated 3D reference volume 850 is then used in a training workflow 860 (e.g., the training workflow discussed with reference to FIG. 6).

Additionally, in a treatment workflow 870 (e.g., the treatment workflow discussed with reference to FIG. 5), the same-contrast 2D templates 822 can be used as registration targets for feature extraction from the 2D images. The calculated offset 830, provided from the registration results, is used within the treatment workflow 870 to compute the true relative motion parameters (relative to the primary (non-updated) 3D reference volume 810).

Figure 9:
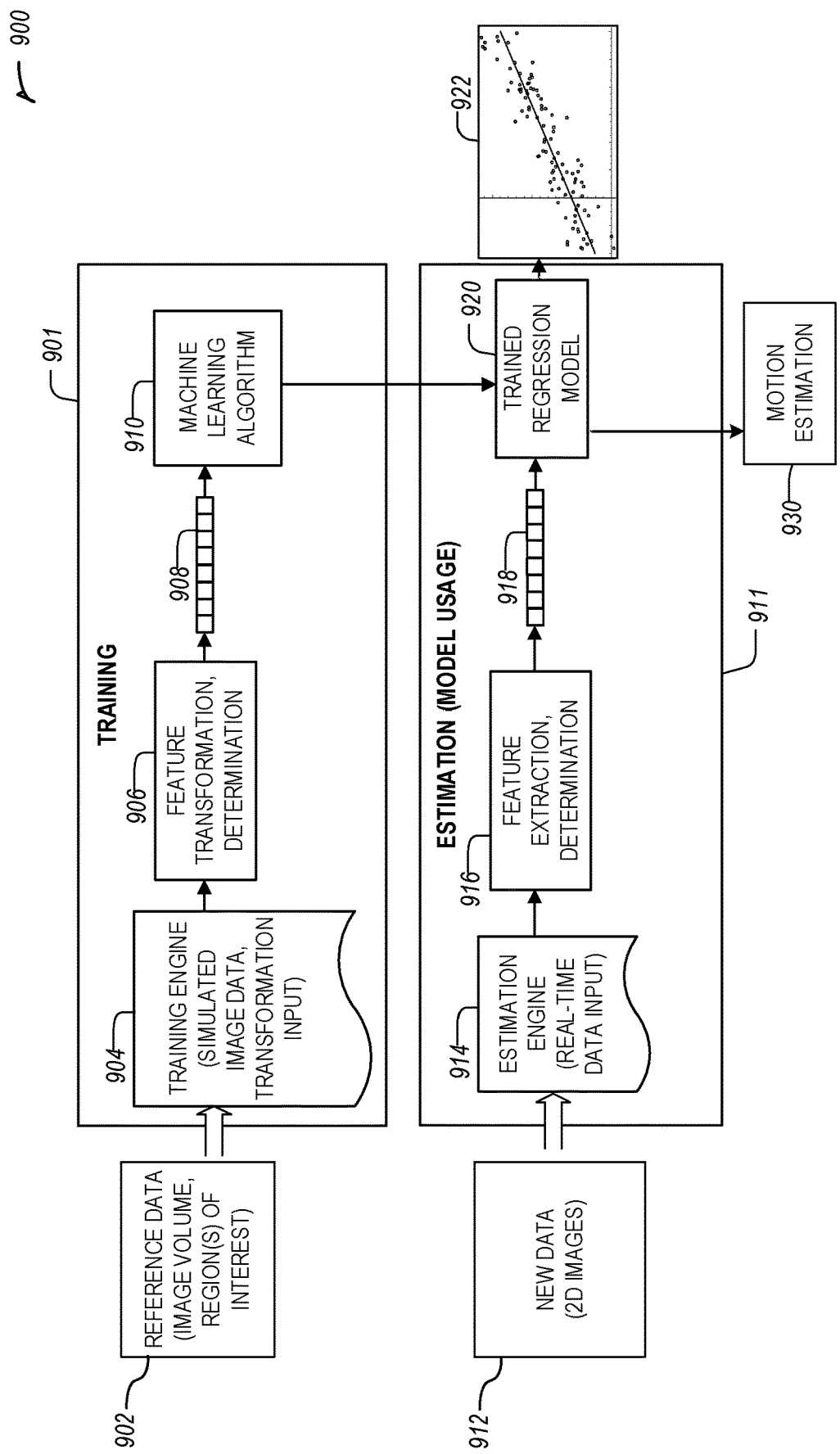
FIG. 9 illustrates a regression machine learning workflow for use in estimating patient motion during a radiotherapy session, according to some examples.

FIG. 9 illustrates a regression machine learning workflow 900 for use in estimating patient motion during a radiotherapy session. The machine learning workflow 900 includes a training workflow 901 and an estimation workflow 911 to perform training and estimation operations, respectively. The workflow 900 provides another view of data processing occurring with the training and treatment aspects depicted in FIG. 8. It will be understood that the training workflow 901 may incorporate the training aspects discussed with FIGS. 6 and 7, above, and the estimation workflow may incorporate the motion estimation aspects discussed with FIG. 5, above.

In the training workflow 901, training engine 904 generates training inputs from transformed image data (e.g., motion-transformed reference image data 902), to produce features 908 for training. Feature transformation and determination 906 determines one or more image and motion features 908 from the reference data input, such as with use of the transformation workflow depicted in FIG. 6. Stated generally, the image and motion features 908 provide a set of the information input and include information determined to be indicative of a particular outcome. The machine learning algorithm 910 (e.g., a regression algorithm) produces a trained model 920 (e.g., a regression model) based upon the image and motion features 908 and the correspondence between image characteristics and the known image transformation (motion). The regression model 920 thus learns the relationship between features of the simulated image data (2D image(s)) and the relative motion parameters (relative to a 3D reference volume).

In the estimation workflow 911, newly captured data 912 (e.g., a 2D image of a patient captured in real time) may be input to the estimation engine 914. The estimation engine 914 operates to identify a region of interest (if applicable) and use a feature determination engine 916 to determine image features of the newly captured data 912 that are relevant to a corresponding patient state. The feature determination engine 916 produces image features 918, which are input into the regression model 920. The training workflow 901 may operate in an offline manner to train the regression model 920, such that weights of the regression model 920 are learned during training and fixed. Then, during the estimation workflow 911, the image features 918 are input into the trained regression model 920, which internally uses the fixed weights to produce the motion estimation 930. The estimation engine 914, however, may be designed to operate in an online manner. It should be noted that the regression model 920 may be periodically updated via additional training or user feedback (e.g., additional, changed, or removed measurements or patient states).

The machine learning algorithm 910 may be selected from among many different potential supervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models. A representation of the regression model is illustrated in block 922, showing an example linear regression. If a linear regressor is used, the model parameters (e.g., weights or coefficients) represent the importance of each of the corresponding features. However, with use of non-linear regressors, such as regression trees or random forests, the model parameters are not directly related to feature importance.

The machine learning algorithm 910 trains the model 920 as described herein, based on how motion represented by image transformation correspond to image data. In an example, the machine learning algorithm 910 implements a regression problem (e.g., linear, polynomial, regression trees, kernel density estimation, support vector regression, random forests implementations, or the like). The resulting training parameters define the regression model (a generator) as a correspondence motion model for the chosen machine learning algorithm.

In the conventional LINAC case, this training may be performed separately for every possible gantry angle (e.g., with a one degree increment), since x-ray acquisition orientation may be constrained to an orthogonal angle with respect to the treatment beam. In the MR-LINAC case, control may be given to a clinician on the 2D acquisition plane for position or orientation. Repeating cross-validation on training data with different choice of 2D planes can reveal which 2D planes yield best surrogate information for a given patient/tumor site.

After the machine learning algorithm has performed training and the trained regression model is aligned to the patient, instantaneous images are acquired as the radiotherapy treatment beam is controlled, before and after treatment. For each received image, the process may include identifying motion estimation 930 of a region of interest using the model 920, and using such estimated relative motion to provide other motion estimation of the region of interest, the treatment area(s), and the patient.

FIG. 10 illustrates a flowchart 1000 of a method of training a regression machine learning model for generating estimated motion in a region of interest, incorporating the techniques discussed above. For instance, the following features of flowchart 1000 may be integrated or adapted with the training discussed with reference to FIG. 6.

Operation 1010 includes obtaining three-dimensional image data corresponding to a human subject for radiotherapy treatment (e.g., the image data including the reference volume and at least one region of interest(s) to track). In an example, a reference volume represents the patient anatomy in three dimensions, and the at least one region of interest is defined within the three dimensions.

Operation 1020 follows, which includes identifying image transformation parameters defining a spatial transformation (e.g., rotation and/or translation). At operation 1030, the spatial transformation is applied to the reference volume (imaging data). This is followed by operation 1040, which includes performing slicing on the transformed reference volume and region of interest, to produce two-dimensional synthetic images for training. Operation 1050 follows with extracting respective sets of features from the two-dimensional synthetic images. In further examples, the feature extraction includes generating multi-orientation feature vectors, based on the extracted sets of features. After operations 1020-1050, pairs of multi-orientation feature vectors and corresponding spatial transformations are established for training.

Operation 1060 includes training a machine learning regression model with the pairs of image transformation parameters and corresponding features (e.g., pairs of multi-orientation feature vectors and corresponding spatial transformations, that were obtained from the two-dimensional synthetic images). Operations 1020-1050 are repeated, as necessary, for generating a set of training data which can be used to train (or fit) the regressor model.

Operation 1070 concludes the flowchart 1000 by providing a trained machine learning regression model for use with a radiotherapy treatment session, such as is discussed with reference to the model usage examples herein.

FIG. 11 illustrates a flowchart 1100 of a method of using a trained regression machine learning model, for estimating movement in a region of interest, based on the techniques discussed above. For instance, the following features of flowchart 1000 may be integrated or adapted with the model usage discussed with reference to FIG. 5.

Operation 1110 begins with obtaining three-dimensional image data corresponding to a human subject, at a tracking region of interest (prior to radiotherapy session). This is followed by operation 1120, involving training a machine learning regression model based on the three-dimensional image data corresponding to the subject. For instance, operations 1110, 1120 may be expanded into further training actions as depicted with reference to flowchart 1000 or the training functions in FIG. 6.

Operation 1130 includes obtaining real-time, two-dimensional image data corresponding to subject, captured on an ongoing basis during a radiotherapy session. The two-dimensional image data may capture at least a portion of the region of interest, and may include a first two-dimensional image captured at a first orientation and a second two-dimensional image captured at a second orientation (with additional orientations and images also possible). In some examples, the first two-dimensional image is captured at a first time during the radiotherapy treatment session and the second two-dimensional image is captured at a second time during the radiotherapy treatment session (e.g., within 300 milliseconds, or according to another time duration which enables real-time motion processing).

Operation 1140 (optional, as applicable) includes converting two-dimensional image data to match a contrast of three-dimensional image data. For instance, this may incorporate the features of FIG. 8 or the accompanying examples, which discusses techniques applicable where the three-dimensional reference volume is acquired with a first MR pulse acquisition sequence, but the two-dimensional image data is acquired with a second, different MR pulse acquisition sequence.

Operation 1150 includes extraction of the features from the real-time, two-dimensional image data. In an example, an extracted first set of features from a first image and a second set of features from a second image are combined into a multi-dimensional feature vector. The features may be extracted within a region of interest or other designated areas of the image(s). In specific examples, the extracted features are obtained after performing deformable image registration and dimensionality reduction techniques, as discussed above.

Operation 1160 includes analysis of extracted features with the trained machine learning regression model (e.g., trained in operation 1120), that has been trained to estimate transformation parameters describing the relative motion of the region of interest. This relative motion is relative to the region of interest imaged in the original three-dimensional image data. The trained machine learning regression model may accept the multi-dimensional feature vector as input, and produce values indicating a spatial transformation of the extracted features as output.

Operation 1170 provides the output from the trained machine learning regression model, the output indicating indicates a relative motion estimation of the region of interest in the anatomy of the human subject. Based on this output, operation 1180 may be performed to control a radiotherapy treatment based on the relative motion estimation, using the radiotherapy control techniques discussed herein.

FIG. 12 is a flowchart 1200 illustrating example operations for performing training and treatment workflows (including those depicted among FIGS. 4 to 11), according to various examples. These operations may be implemented at processing hardware of the image processing computing system 110, for instance.

At operation 1210, image processing computing system 110 obtains (or captures, or causes an imaging modality to capture) three-dimensional image data, including radiotherapy constraints and targets, corresponding to a human subject. As discussed above, this may be obtained prior to radiotherapy treatment, and include three-dimensional magnetic resonance (MR) volume or a three-dimensional computed tomography (CT) volume.

At operation 1220, the image processing computing system 110 obtains (or captures, or causes an imaging modality to capture) two-dimensional image data, on an ongoing basis, to capture movement of the subject with multi-orientation images.

At operation 1230, the real-time two-dimensional imaging data is pre-processed for use with the model, such as to extract features from multi-orientation two-dimensional images. At operation 1240, the image processing computing system 110 uses a trained regression model (trained such as discussed with reference to FIG. 10) to estimate spatial transformation from extracted features, and generate estimated real-time movement (such as discussed with reference to FIG. 11).

At operation 1250, the image processing computing system 110 identifies a movement state of subject, based on the estimated real-time movement. This may be accompanied by operations (sequentially or in parallel), such as operation 1260, which utilizes the image processing computing system 110 to locate a radiation therapy target within subject using the identified movement state, or operation 1270, which utilizes the image processing computing system 110 to track a radiation therapy target within subject in real-time using the identified movement state.

At operation 1280, image processing computing system 110 directs or controls radiation therapy, using a treatment machine, to the radiation therapy target according to the identified movement state. It will be understood that a variety of existing approaches for modifying or adapting radiotherapy treatment may occur based on the controlled therapy or identified movement state, once correctly estimated.

The processes depicted in flowcharts 1000, 1100, 1200 with FIGS. 10 to 12 may be embodied in computer-readable instructions for execution by one or more processors such that the operations of the process may be performed, for instance, in part or in whole by the functional components of the image processing computing system 110. However, in other examples, at least some of the operations of the process may be deployed on various other hardware configurations. Some or all of the operations of process can be in parallel, out of order, or entirely omitted.

FIG. 13 illustrates a block diagram of an example of a machine 1300 on which one or more of the methods as discussed herein can be implemented. In one or more examples, one or more items of the image processing computing system 110 can be implemented by the machine 1300. In alternative examples, the machine 1300 operates as a standalone device or may be connected (e.g., networked) to other machines. In one or more examples, the image processing computing system 110 can include one or more of the items of the machine 1300. In a networked deployment, the machine 1300 may operate in the capacity of a server or a client machine in server-client network environment, or as a peer machine in a peer-to-peer (or distributed) network environment. The machine may be a personal computer (PC), server, a tablet, smartphone, a web appliance, edge computing device, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1300 includes processing circuitry or processor 1302 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 1321 (e.g., a transducer that converts one form of energy (e.g., light, heat, electrical, mechanical, or other energy) to another form of energy), or the like, or a combination thereof), a main memory 1304 and a static memory 1306, which communicate with each other via a bus 1308. The machine 1300 (e.g., computer system) may further include a video display device 1310 (e.g., a liquid crystal display (LCD) or a cathode ray tube (CRT)). The machine 1300 also includes an alphanumeric input device 1312 (e.g., a keyboard), a user interface (UI) navigation device 1314 (e.g., a mouse), a disk drive or mass storage unit 1316, a signal generation device 1318 (e.g., a speaker), and a network interface device 1320.

The disk drive unit 1316 includes a machine-readable medium 1322 on which is stored one or more sets of instructions and data structures (e.g., software) 1324 embodying or utilized by any one or more of the methodologies or functions described herein. The instructions 1324 may also reside, completely or at least partially, within the main memory 1304 and/or within the processor 1302 during execution thereof by the machine 1300, the main memory 1304 and the processor 1302 also constituting machine-readable media.

The machine 1300 as illustrated includes an output controller 1328. The output controller 1328 manages data flow to/from the machine 1300. The output controller 1328 is sometimes called a device controller, with software that directly interacts with the output controller 1328 being called a device driver.

While the machine-readable medium 1322 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and 4G/5G data networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMs, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In an embodiment, the computer-readable storage medium may have encoded a data structure for treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, C#, Java, Python, CUDA programming, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A computer-implemented method for monitoring anatomic position of a human subject for a radiotherapy treatment session, the method comprising:
    obtaining three-dimensional image data corresponding to the subject, the three-dimensional image data including: a reference volume that represents anatomy of the subject in three dimensions, at least one region of interest defined within the three dimensions, and an intermediate three-dimensional reference volume captured prior to the radiotherapy treatment session;
    performing a registration of the intermediate three-dimensional reference volume to the reference volume;
    obtaining two-dimensional image data corresponding to the subject, the two-dimensional image data captured during the radiotherapy treatment session, and the two-dimensional image data capturing at least a portion of the at least one region of interest;
    extracting features from the two-dimensional image data;
    providing the extracted features as input to a machine learning regression model, the machine learning regression model trained to estimate a spatial transformation in the three dimensions of the reference volume from the features extracted from the two-dimensional image data, wherein analysis of the extracted features by the machine learning regression model includes use of the registration; and
    obtaining, from output of the machine learning regression model, a relative motion estimation of the at least one region of interest, wherein the relative motion estimation indicates motion relative to the reference volume which is estimated from the extracted features.

2. The method of claim 1, wherein the two-dimensional image data comprises a first two-dimensional image captured at a first orientation and a second two-dimensional image captured at a second orientation, and wherein the features extracted from the two-dimensional image data include a first set of features extracted from the first two-dimensional image and a second set of features extracted from the second two-dimensional image.

3. The method of claim 2, wherein the first two-dimensional image is captured from a first plane, and wherein the second two-dimensional image is captured from a second plane that is orthogonal to the first plane.

4. The method of claim 2, wherein the first two-dimensional image is captured at a first time during the radiotherapy treatment session and wherein the second two-dimensional image is captured at a second time during the radiotherapy treatment session.

5. The method of claim 4, wherein the second time occurs within 300 milliseconds after the first time.

6. The method of claim 2, wherein the first set of features and the second set of features are combined into a multi-dimensional feature vector, and wherein the machine learning regression model is trained to process the multi-dimensional feature vector as input.

7. The method of claim 6, wherein the extracting of the first set of features and the second set of features comprises extracting respective features within the at least one region of interest.

8. The method of claim 7, wherein the extracting of the respective features within the at least one region of interest comprises:
    performing deformable image registration; and
    performing dimensionality reduction techniques.

9. The method of claim 6, wherein the first and second two-dimensional images are kilovoltage (kV) x-ray projection images, and wherein extracting the first set of features and the second set of features comprises extracting fiducial positions from the respective kV x-ray projection images.

10. The method of claim 1, the method further comprising:
    training the machine learning regression model prior to the radiotherapy treatment session, the training comprising fitting the machine learning regression model with a mapping identified between pairs of image transformation parameters and corresponding multi-orientation features.

11. The method of claim 10, wherein the training comprises:
    applying spatial transformations to the reference volume according to the image transformation parameters;
    generating a plurality of two-dimensional synthetic images from respective slices of the transformed reference volume;
    extracting respective sets of features from the plurality of two-dimensional synthetic images; and
    generating multi-orientation feature vectors, based on the extracted sets of features;
    wherein the training of the machine learning regression model is performed using a plurality of pairs of the multi-orientation feature vectors and the corresponding spatial transformations.

12. The method of claim 11, wherein the spatial transformation includes one or more of translation and rotation, to cause a change in appearance in the at least one region of interest in the reference volume.

13. The method of claim 1, wherein the three-dimensional image data is captured prior to the radiotherapy treatment session, and wherein the three-dimensional image data comprises a three-dimensional magnetic resonance (MR) volume or a three-dimensional computed tomography (CT) volume.

14. The method of claim 1, wherein the two-dimensional image data is magnetic resonance (MR) imaging data, wherein the reference volume is acquired with a first MR pulse acquisition sequence, and wherein the two-dimensional image data is acquired with a second MR pulse acquisition sequence.

15. The method of claim 14,
wherein the intermediate three-dimensional reference volume is captured using the second MR pulse acquisition sequence,
wherein training of the machine learning regression model includes use of the registration.

16. The method of claim 1, further comprising:
performing a radiotherapy treatment with a radiotherapy machine, using the relative motion estimation of the at least one region of interest, wherein performing the radiotherapy treatment comprises at least one of:
changing a position of a radiotherapy beam provided in the radiotherapy treatment, based on the relative motion estimation;
changing a shape of a radiotherapy beam provided in the radiotherapy treatment, based on the relative motion estimation; or
gating a radiotherapy beam provided in the radiotherapy treatment, based on the relative motion estimation.

17. A computer-implemented method for monitoring anatomic position of a human subject for a radiotherapy treatment session, the method comprising:
obtaining three-dimensional image data corresponding to the subject, the three-dimensional image data including: a reference volume that represents anatomy of the subject in three dimensions, and at least one region of interest defined within the three dimensions;
obtaining two-dimensional image data corresponding to the subject, the two-dimensional image data captured during the radiotherapy treatment session, and the two-dimensional image data capturing at least a portion of the at least one region of interest, wherein the two-dimensional image data is magnetic resonance (MR) imaging data, wherein the reference volume is acquired with a first MR pulse acquisition sequence, and wherein the two-dimensional image data is acquired with a second MR pulse acquisition sequence;
obtaining image templates from additional two-dimensional image data corresponding to the subject, the additional two-dimensional image data obtained using the second MR pulse acquisition sequence prior to the radiotherapy treatment session;
performing a registration of the image templates to the reference volume, to determine an offset between the image templates and the reference volume; and
modifying the three-dimensional image data based on the offset, wherein a machine learning regression model is trained to use regression with the modified three-dimensional image data;
extracting features from the two-dimensional image data, wherein extracting features from the two-dimensional image data includes use of the image templates as registration targets for feature extraction;
providing the extracted features as input to the machine learning regression model, the machine learning regression model trained to estimate a spatial transformation in the three dimensions of the reference volume from features extracted from the two-dimensional image data; and
obtaining, from output of the machine learning regression model, a relative motion estimation of the at least one region of interest, wherein the relative motion estimation indicates motion relative to the reference volume which is estimated from the extracted features, wherein the relative motion estimation of the at least one region of interest includes use of the offset.

18. A computing system for monitoring anatomic position of a human subject for a radiotherapy treatment session, the system comprising:
one or more memory devices to store a three-dimensional set of image data corresponding to a subject of radiotherapy treatment, the three-dimensional set of image data including: a reference volume that represents anatomy of the subject in three dimensions, at least one region of interest defined within the three dimensions, and an intermediate three-dimensional reference volume captured prior to the radiotherapy treatment session; and
one or more processors configured to perform operations to:
perform a registration of the intermediate three-dimensional reference volume to the reference volume:
obtain two-dimensional image data corresponding to the subject, the two-dimensional image data captured during the radiotherapy treatment session, and the two-dimensional image data capturing at least a portion of the at least one region of interest;
extract features from the two-dimensional image data;
provide the extracted features as input to a machine learning regression model, the machine learning regression model trained to estimate a spatial transformation in the three dimensions of the reference volume from the features extracted from the two-dimensional image data, wherein analysis of the extracted features by the machine learning regression model includes use of the registration; and
obtain, from output of the machine learning regression model, a relative motion estimation of the at least one region of interest, wherein the relative motion estimation indicates motion relative to the reference volume which is estimated from the extracted features.

19. The computing system of claim 18, wherein the two-dimensional image data comprises a first two-dimensional image captured at a first orientation and a second two-dimensional image captured at a second orientation,
wherein the features extracted from the two-dimensional image data include a first set of features extracted from the first two-dimensional image and a second set of features extracted from the second two-dimensional image, and
wherein the first two-dimensional image is captured at a first time during the radiotherapy treatment session and wherein the second two-dimensional image is captured at a second time during the radiotherapy treatment session.

20. The computing system of claim 19, wherein the first set of features and the second set of features are combined into a multi-dimensional feature vector,
- wherein the machine learning regression model is trained to process the multi-dimensional feature vector as input, and
- wherein the extracting of the first set of features and the second set of features comprises extracting respective features within the at least one region of interest by performing deformable image registration and performing dimensionality reduction techniques.

21. A non-transitory computer-readable storage medium comprising computer-readable instructions for monitoring anatomic position of a human subject for a radiotherapy treatment session, wherein the instructions, when executed with a computing machine, cause the computing machine to perform operations comprising:
- obtaining three-dimensional image data corresponding to the subject, the three-dimensional image data including: a reference volume that represents anatomy of the subject in three dimensions, at least one region of interest defined within the three dimensions, and an intermediate three-dimensional reference volume captured prior to the radiotherapy treatment session:
- performing a registration of the intermediate three-dimensional reference volume to the reference volume;
- obtaining two-dimensional image data corresponding to the subject, the two-dimensional image data captured during the radiotherapy treatment session, and the two-dimensional image data capturing at least a portion of the at least one region of interest;
- extracting features from the two-dimensional image data;
- providing the extracted features as input to a machine learning regression model, the machine learning regression model trained to estimate a spatial transformation in the three dimensions of the reference volume from the features extracted from the two-dimensional image data, wherein analysis of the extracted features by the machine learning regression model includes use of the registration; and
- obtaining, from output of the machine learning regression model, a relative motion estimation of the at least one region of interest, wherein the relative motion estimation indicates motion relative to the reference volume which is estimated from the extracted features.

22. The computer-readable storage medium of claim 21, wherein the two-dimensional image data comprises a first two-dimensional image captured at a first orientation and a second two-dimensional image captured at a second orientation,
- wherein the features extracted from the two-dimensional image data include a first set of features extracted from the first two-dimensional image and a second set of features extracted from the second two-dimensional image, and
- wherein the first two-dimensional image is captured at a first time during the radiotherapy treatment session and wherein the second two-dimensional image is captured at a second time during the radiotherapy treatment session.

23. The computer-readable storage medium of claim 22, wherein the first set of features and the second set of features are combined into a multi-dimensional feature vector,
- wherein the machine learning regression model is trained to process the multi-dimensional feature vector as input, and
- wherein the extracting of the first set of features and the second set of features comprises extracting respective features within the at least one region of interest by performing deformable image registration and performing dimensionality reduction techniques.

* * * * *

UNITED STATES PATENT AND TRADEMARK OFFICE
CERTIFICATE OF CORRECTION

PATENT NO. : 12,133,993 B2
APPLICATION NO. : 17/302252
DATED : November 5, 2024
INVENTOR(S) : Novosad et al.

Page 1 of 1

It is certified that error appears in the above-identified patent and that said Letters Patent is hereby corrected as shown below:

In the Claims

In Column 32, Line 32, in Claim 18, delete "volume:" and insert --volume;-- therefor In Column 33, Line 24, in Claim 21, delete "session:" and insert --session;-- therefor Signed and Sealed this
Thirtieth Day of September, 2025

John A. Squires
*Director of the United States Patent and Trademark Office*